(12) United States Patent
Myllyoja et al.

(10) Patent No.: US 12,203,035 B2
(45) Date of Patent: Jan. 21, 2025

(54) PROCESS FOR THE MANUFACTURE OF DIESEL RANGE HYDROCARBONS

(71) Applicant: NESTE OYJ, Espoo (FI)

(72) Inventors: Jukka Myllyoja, Vantaa (FI); Pekka Aalto, Porvoo (FI); Pekka Savolainen, Vantaa (FI); Veli-Matti Purola, Hamari (FI); Ville Alopaeus, Espoo (FI); Johan Gronqvist, Porvoo (FI)

(73) Assignee: Neste Oyj, Espoo (FI)

( * ) Notice: Subject to any disclaimer, the term of this patent is extended or adjusted under 35 U.S.C. 154(b) by 129 days.

(21) Appl. No.: 17/930,148

(22) Filed: Sep. 7, 2022

(65) Prior Publication Data
US 2023/0014266 A1    Jan. 19, 2023

Related U.S. Application Data

(60) Continuation of application No. 17/015,639, filed on Sep. 9, 2020, now Pat. No. 11,473,018, which is a
(Continued)

(51) Int. Cl.
*C10G 3/00* (2006.01)
*C07C 1/24* (2006.01)
(Continued)

(52) U.S. Cl.
CPC .................. *C10G 3/50* (2013.01); *C07C 1/24* (2013.01); *C07C 5/03* (2013.01); *C07C 5/22* (2013.01);
(Continued)

(58) Field of Classification Search
CPC ... C10G 3/42; C10G 3/50; C10G 3/60; C10G 2300/1011; C10G 2300/1014; C10G 2300/1018; C07C 5/22; B01J 19/245
See application file for complete search history.

(56) References Cited

U.S. PATENT DOCUMENTS 2,093,159 A    9/1937  Schmidt
2,482,760 A    9/1949  Goebel
(Continued)

FOREIGN PATENT DOCUMENTS

CA    1313200    1/1993
CA    2149685    9/1999
(Continued)

OTHER PUBLICATIONS

Action Closing Prosecution in Reexamination Control No. 95/002,084, mailed Jun. 26, 2013.
(Continued)

*Primary Examiner* — Yate' K Cutliff
(74) *Attorney, Agent, or Firm* — Finnegan, Henderson, Farabow, Garrett & Dunner LLP

(57) ABSTRACT

The invention relates to a process for the manufacture of diesel range hydrocarbons wherein a feed is hydrotreated in a hydrotreating step and isomerised in an isomerisation step, and a feed comprising fresh feed containing more than 5 wt % of free fatty acids and at least one diluting agent is hydrotreated at a reaction temperature of 200-400° C., in a hydrotreating reactor in the presence of catalyst, and the ratio of the diluting agent/fresh feed is 5-30:1.

15 Claims, 8 Drawing Sheets

Related U.S. Application Data continuation of application No. 16/715,871, filed on Dec. 16, 2019, now Pat. No. 10,800,976, which is a continuation of application No. 16/039,210, filed on Jul. 18, 2018, now Pat. No. 10,550,332, which is a continuation of application No. 15/428,080, filed on Feb. 8, 2017, now Pat. No. 10,059,887, which is a continuation of application No. 14/477,758, filed on Sep. 4, 2014, now Pat. No. 9,598,327, which is a continuation of application No. 13/491,182, filed on Jun. 7, 2012, now Pat. No. 8,859,832, which is a continuation of application No. 13/107,146, filed on May 13, 2011, now Pat. No. 8,212,094, which is a division of application No. 11/477,922, filed on Jun. 30, 2006, now Pat. No. 8,022,258.

(60) Provisional application No. 60/695,853, filed on Jul. 5, 2005.

(51) Int. Cl.
| | |
|---|---|
| *C07C 5/03* | (2006.01) |
| *C07C 5/22* | (2006.01) |
| *C07C 5/27* | (2006.01) |
| *C07C 7/10* | (2006.01) |
| *C07C 7/12* | (2006.01) |
| *C07C 7/13* | (2006.01) |
| *C10G 45/02* | (2006.01) |
| *C10G 45/58* | (2006.01) |
| *C10G 45/62* | (2006.01) |
| *C10G 45/64* | (2006.01) |
| *C10G 65/04* | (2006.01) |
| *C10L 1/08* | (2006.01) |

(52) U.S. Cl.
CPC .............. *C07C 5/27* (2013.01); *C07C 5/2775* (2013.01); *C07C 7/10* (2013.01); *C07C 7/12* (2013.01); *C07C 7/13* (2013.01); *C10G 3/42* (2013.01); *C10G 3/46* (2013.01); *C10G 3/47* (2013.01); *C10G 45/02* (2013.01); *C10G 45/58* (2013.01); *C10G 45/62* (2013.01); *C10G 45/64* (2013.01); *C10G 65/043* (2013.01); *C10L 1/08* (2013.01); *C07C 2529/076* (2013.01); *C10G 2300/1011* (2013.01); *C10G 2300/1014* (2013.01); *C10G 2300/1018* (2013.01); *C10G 2300/202* (2013.01); *C10G 2300/205* (2013.01); *C10G 2300/207* (2013.01); *C10G 2300/4006* (2013.01); *C10G 2300/4081* (2013.01); *C10G 2300/802* (2013.01); *C10G 2400/04* (2013.01); *Y02E 50/10* (2013.01); *Y02P 30/20* (2015.11)

(56) References Cited

U.S. PATENT DOCUMENTS

| | | | |
|---|---|---|---|
| 2,482,761 | A | 9/1949 | Goebel |
| 2,664,429 | A | 12/1953 | Goebel |
| 2,793,219 | A | 5/1957 | Barrett et al. |
| 2,798,220 | A | 5/1957 | Barrett et al. |
| 3,144,404 | A | 8/1964 | Tyson |
| 3,147,210 | A | 9/1964 | Hass et al. |
| 3,487,011 | A | 12/1969 | Henke et al. |
| 3,764,516 | A | 10/1973 | Steinmetz et al. |
| 3,898,153 | A | 8/1975 | Louder et al. |
| 3,929,615 | A | 12/1975 | Linden et al. |
| 4,049,686 | A | 9/1977 | Ringers et al. |
| 4,151,072 | A | 4/1979 | Nowack et al. |
| 4,300,009 | A | 11/1981 | Haag et al. |
| 4,419,220 | A | 12/1983 | LaPierre et al. |
| 4,431,524 | A | 2/1984 | Norman |
| 4,432,865 | A | 2/1984 | Norman |
| 4,440,871 | A | 4/1984 | Lok et al. |
| 4,512,878 | A | 4/1985 | Reid et al. |
| 4,518,485 | A | 5/1985 | LaPierre et al. |
| 4,554,397 | A | 11/1985 | Stern et al. |
| 4,655,906 | A | 4/1987 | Bjornson et al. |
| 4,788,378 | A | 11/1988 | Chang et al. |
| 4,859,311 | A | 8/1989 | Miller |
| 4,960,960 | A | 10/1990 | Harrison et al. |
| 4,992,403 | A | 2/1991 | Takahashi et al. |
| 4,992,605 | A | 2/1991 | Craig et al. |
| 5,093,535 | A | 3/1992 | Harrison et al. |
| 5,135,638 | A | 8/1992 | Miller |
| 5,158,982 | A | 10/1992 | Stapp |
| 5,169,813 | A | 12/1992 | Miller et al. |
| 5,183,556 | A | 2/1993 | Reilly et al. |
| 5,292,428 | A | 3/1994 | Harrison et al. |
| 5,298,639 | A | 3/1994 | Toeneboehn et al. |
| 5,346,724 | A | 9/1994 | Ohgake et al. |
| 5,475,160 | A | 12/1995 | Singleton et al. |
| 5,578,090 | A | 11/1996 | Bradin |
| 5,578,091 | A | 11/1996 | Jackson et al. |
| 5,612,273 | A | 3/1997 | Prada et al. |
| 5,688,749 | A | 11/1997 | Ibuki et al. |
| 5,705,722 | A | 1/1998 | Monnier et al. |
| 5,814,109 | A | 9/1998 | Cook |
| 5,817,595 | A | 10/1998 | Tejada et al. |
| 5,861,441 | A | 1/1999 | Waycuilis |
| 5,882,505 | A | 3/1999 | Wittenbrink et al. |
| 5,888,376 | A | 3/1999 | Wittenbrink et al. |
| 5,906,729 | A | 5/1999 | Chou |
| 5,951,848 | A | 9/1999 | Baker et al. |
| 6,051,127 | A | 4/2000 | Moureaux |
| 6,123,835 | A | 9/2000 | Ackerson et al. |
| 6,174,501 | B1 | 1/2001 | Noureddini |
| 6,187,903 | B1 | 2/2001 | Elsasser et al. |
| 6,203,695 | B1 | 3/2001 | Harle et al. |
| 6,296,759 | B1 | 10/2001 | Vaarkamp et al. |
| 6,399,845 | B1 | 6/2002 | Raulo et al. |
| 6,524,994 | B1 | 2/2003 | Reesink et al. |
| 7,550,634 | B2 | 6/2009 | Yao et al. |
| 8,022,258 | B2 | 9/2011 | Myllyoja et al. |
| 8,212,094 | B2 | 7/2012 | Myllyoja et al. |
| 8,278,492 | B2 | 10/2012 | Myllyoja et al. |
| 2001/0027937 | A1 | 10/2001 | Tsao et al. |
| 2002/0027937 | A1 | 3/2002 | Govorkov et al. |
| 2002/0062055 | A1 | 5/2002 | Raulo et al. |
| 2004/0055209 | A1 | 3/2004 | Jakkula et al. |
| 2004/0230085 | A1 | 11/2004 | Jakkula et al. |
| 2005/0060929 | A1 | 3/2005 | Caprotti et al. |
| 2005/0218039 | A1 | 10/2005 | Kalnes |
| 2006/0112614 | A1 | 6/2006 | Davenport et al. |
| 2006/0207166 | A1 | 9/2006 | Herskowitz et al. |
| 2006/0264684 | A1 | 11/2006 | Petri et al. |
| 2007/0010682 | A1 | 1/2007 | Myllyoja et al. |
| 2007/0068848 | A1 | 3/2007 | Monnier et al. |
| 2011/0282116 | A1 | 11/2011 | Myllyoja et al. |
| 2013/0030229 | A1 | 1/2013 | Myllyoja et al. |
| 2021/0054292 | A1* | 2/2021 | Laohakunakorn ....... C10G 3/46 |

FOREIGN PATENT DOCUMENTS

| | | |
|---|---|---|
| CA | 2316141 | 2/2001 |
| CA | 2400944 | 8/2001 |
| CZ | 283 575 | 2/1998 |
| DE | 4116905 | 8/1992 |
| EP | 0 168 091 A1 | 1/1986 |
| EP | 0 378 887 B1 | 9/1995 |
| EP | 0 794 241 A2 | 9/1997 |
| EP | 1 396 531 A2 | 3/2004 |
| EP | 1 398 364 A1 | 3/2004 |
| EP | 1 489 157 A1 | 12/2004 |
| EP | 1 396 531 B1 | 3/2007 |
| EP | 1 984 420 B1 | 7/2013 |
| FI | 933982 | 9/1993 |
| FI | 95391 | 9/1995 |
| FI | 100248 | 10/1997 |
| FI | 20021595 | 3/2004 |

(56) References Cited

FOREIGN PATENT DOCUMENTS

| | | |
|---|---|---|
| FR | 2 151 059 | 4/1973 |
| FR | 2 607 803 | 6/1988 |
| GB | 1002922 | 9/1965 |
| GB | 1524781 | 9/1978 |
| GB | 2090611 | 7/1982 |
| IE | 921671 | 12/1995 |
| JP | 59-108088 | 6/1984 |
| JP | 2003-171670 A | 6/2003 |
| SE | 9700149 | 8/1997 |
| SE | 520 633 | 8/2003 |
| WO | WO 1992/16601 A1 | 10/1992 |
| WO | WO 1995/25152 | 9/1995 |
| WO | WO 1996/18705 | 6/1996 |
| WO | WO 1998/56876 | 12/1998 |
| WO | WO 2000/29512 | 5/2000 |
| WO | WO 2001/12581 | 2/2001 |
| WO | WO 2001/49812 | 7/2001 |
| WO | WO 2003/022960 | 3/2003 |
| WO | WO 2004/022674 | 3/2004 |
| WO | WO 2007/033460 | 3/2007 |

OTHER PUBLICATIONS

"Albemarle, ExxonMobil Scientists Named 'Heroes of Chemistry' for 'Nebula' ULSD Catalyst Development," Diesel Fuel News, vol. 12, No. 17 (Sep. 1, 2008), Ex. 1079 served but not filed in *Syntroleum v. Neste*—IPR 2013-00178.
"Alternative Energy Sources for Potential Community Use," Community Energy Systems Group (CES Group), CETC-CANMET (Mar. 2003).
"Hydrotreating Catalyst In-Situ Presulphiding Guidelines—Liquid Phase (preferred method)—Gas Phase (alternative method), Criterion Catalysts," Technical Bulletin, Aug. 1998.
Adams, T., et al., "A Demonstration of Fat and Grease as Industrial Boiler Fuel," http://fatforfuel.us/images/UofGAStudy.pdf, Jun. 30, 2002.
Akzo Nobel Presentation, 2003 (63 pages), Exhibit 1068 in *Syntroleum v. Neste* IPR2013-00178.
Alencar et al., 31 J. Agric. Food Chem., 1983, pp. 1268-1270, Exhibit 1066 in *Syntroleum v. Neste* IPR2013-00178.
Ali, Y., et al. "Fuel Properties of Tallow and Soybean Oil Esters," JAOCS, vol. 72, No. 12 (1995).
Amended Petition dated Mar. 21, 2013 in Inter Partes Review No. IPR2013-00178.
Amended Petition for Inter Partes Review of U.S. Pat. No. 8,278,492 filed Dec. 13, 2013 (IPR 2014-00192) (Paper No. 15).
Amended Petition for Inter Partes Review of U.S. Pat. No. 8,278,492 filed Dec. 13, 2013 (IPR 2014-00192) (Paper No. 16).
Amendment in Response to Non-Final Office Action filed dated Feb. 18, 2009 in U.S. Appl. No. 11/477,921 (Ex. 2022 in IPR2014-00192 for U.S. Pat. No. 8,278,492).
Amendment Under 37 C.F.R. § 1.111 dated Jan. 27, 2012 in U.S. Appl. No. 11/477,921 (Ex. 2023 in IPR2014-00192 for U.S. Pat. No. 8,278,492).
American Heritage College Dictionary, 826 (3d ed. 1997).
Arca, M. et al., 89 J. Am. Oil Chem. Soc., 2012, pp. 987-994, Exhibit 1058 in *Syntroleum v. Neste* IPR2013-00178.
Arizona Chemical Website http://www.arizonachemical.com/Products/Refinery-Products/Tall-Oil-Fatty-Acids/, "Tall Oil Fatty Acids" (last accessed Oct. 17, 2013), Neste Exhibit 2014 in *Syntroleum v. Neste* IPR2013-00178.
Bartholomew, C.H. & Farrauto, Fundamentals of Industrial Catalytic Processes (John Wiley & Sons, Inc. 2006), p. 16, Ex. 1087 in *Syntroleum v. Neste*—IPR 2013-00178.
Bartholomew, C.H., Fundamentals of Industrial Catalytic Processes, Blackie Academic & Professional, 1997, pp. 562-563 (Ex.1066 in IPR2014-00192).
Bartholomew, Calvin H., "Mechanisms of Catalyst Deactivation," *Applied Catalysis A: General*, 212 (2001): 17-60 (Ex. 2006 in IPR2014-00192 for U.S. Pat. No. 8,278,492).

Bartholomew, C.H. et al., "Sulfur Poisoning of Metals," Advances in Catalysis, 31, 135-242 (1982).
Bauldauf et al., "Processing of Vegetable Oil to Fuels in Mineral Oil Refinery Processes," VDE Reports, No. 1126 (1994) pp. 153-168.
Beare-Rogers, J., et al., "Lexicon of Lipid Nutrition" (IUPAC Technical Report), *Pure Appl. Chem.*, vol. 73, No. 4, pp. 685-744, 2001.
Bergerioux, C. et al, "Determination of Trace Element Pathways in a Petroleum Distillation Unit by Instrumental Neutron Activation Analysis," Journal of Radioanalytical Chemistry, vol. 54, No. 1-2, 1979, pp. 255-265.
Billon, A. et al., Fuels: new approaches. Viewpoint of and proposed solutions from the French Petroleum institute, 1994, Petroe et Techniques, 388, 23-45 (1 page abstract).
Bishop, N. et al., Ukpia: Future Road Fuels (2004).
Biswas, J., Bickle, G. M., Gray, P. G., Do, D. D., & Barbier, J., The role of Deposited Poisons and Crystallite Surface Structure in the Activity and Selectivity of Reforming Catalysts, Catalysis Reviews Science and Engineering, 30(2), 161-247 (1988).
Bradley, T. F. et al., 32 Ind. & Eng. Chem., 1940, pp. 802-809, Exhibit 1057 in *Syntroleum v. Neste* IPR2013-00178.
Bridgwater, A. V., "Catalysis in thermal biomass conversion," Applied Catalysis A: General, 116, 5-47 (1994).
Broderick, D. H. et al., "The Sulfided Co—Mo/$\gamma$-Al$_2$O$_3$ Catalyst: Evidence of Structural Changes during Hydrodesulfurization of Dibenzothiophene," Journal of Catalysis, 54, 94-97 (1978).
Brown, Theodore L., et al., *Chemistry: The Central Science*, pp. 810-815 (Prentice Hall, 7th ed. 1997), Ex. 2039 in *Syntroleum v. Neste* IPR2013-00178.
Busto, M. et al., Simultaneous Hydroconversion of n-Hexane and Benzene over Pt/WO3—ZrO2 in the Presence of Sulfur Impurities, Energy & Fuels 2009, 23, 599-606.
Canola Laboratory Report, Summit Environmental Technologies, issued Feb. 27, 2013.
Canola: Standards and Regulations (from https://canola-council.merchantsecure.com/oil_tech.aspx).
Cecchi, G. et al., "Conversion des huiles végétales en carburants potentiels, Essais préliminaries," Revue Francaise des Corps Gras, No. 9, 397-401 (1987).
Translation of Cecchi, G. et al., "Conversion of Vegetable Oils Into Potential Fuels, Preliminary Trial," Revue Francaise Des Corps Gras, vol. 34, No. 9, Sep. 1987, pp. 397-404.
Chiranjeevi, T. et al., "Effect of Si/Al ratio of HMS support on catalytic functionalities of Mo, CoMo, NiMo hydrotreating catalysts," Catalysis Communications 6, pp. 101-106 (2005).
Clausen, B.S. et al., "Extended X-Ray Absorption Fine Structure Study of Co—Mo Hydrodesulfurization Catalysts," J. Phys. Chem., vol. 85, No. 25, 1981, pp. 3868-3872, Ex. 1076 served but not filed in *Syntroleum v. Neste*—IPR 2013-00178.
Cmolik, J. et al., "Effects of plant-scale alkali refining and physical refining on the quality of rapeseed oil," Eur. J. Lipid Sci. Technol., pp. 15-22 (2000).
Cooper, B. M. et al., "Production of Swedish Class I Diesel Using Duel-Stage Process," Ch. 15 in Catalytic Hydroprocessing of Petroleum and Distillates, 279-290 (1993).
Corma, A., & Martinez A. (1998) "Transformation of Alkanes on Solid Acid and Bifunctional Catalysts" in E.G. Derouane et al. (Eds.), Catalytic Activation and Functionalisation of Light Alkanes: Advances and Challenges (pp. 35-74), Netherlands: Kluwer Academic Publishers, Exhibit 1024 in *Syntroleum v. Neste* IPR2014-00192.
Corrected Petitioner's Motion for Observations in IPR 2013-00178—Feb. 28, 2014.
Cowan, J. C., "Dimer Acids," J. Am. Oil Chemists Soc., vol. 39, 1962, pp. 534-545, Ex. 1073 served but not filed in *Syntroleum v. Neste*—IPR 2013-00178.
Craig, W. and Coxworth, E., "A Marketing Survey of Worldwide Potential for Use of Vegetable Oil Conversion Products in Diesel Fuel," SRC Publication No. R-1520-2-C-89 (Oct. 1989), Neste Exhibit 2021 in *Syntroleum v. Neste* IPR2013-00178.

(56) References Cited

OTHER PUBLICATIONS

Craig, W. et al., "Conversion of Vegetable Oils to Conventional Liquid Fuel Extenders," Biomass Resources, Saskatchewan Research Council, Saskatoon, Saskatchewan, Sixth Canadian Bioenergy R&D Seminar, 1987.
Criterion Catalysts, "Technical Bulletin: Hydrotreating Catalyst In-Situ Presulphiding Guidelines" Aug. 1998, Exhibit 1025 in *Syntroleum v. Neste* IPR2014-00192.
Curriculum Vitae of Dr. Bruce C. Gates, Ph.D., Ex. 2002 in IPR2014-00192 for U.S. Pat. No. 8,278,492 (filed Aug. 18, 2014).
Curriculum Vitae of Dr. Michael T. Klein (2013), Neste Exhibit 2020 in *Syntroleum v. Neste* IPR2013-00178.
Curriculum Vitae of Dr. Nelson E. Lawson, Ph.D. (2013), Neste Exhibit 2013 in *Syntroleum v. Neste* IPR2013-00178.
Curriculum Vitae of Edward Lawrence Sughrue II, Ex. 2031 in *Syntroleum v. Neste* IPR2013-00178.
CV of Edward Sughrue (2013), Exhibit 1039 in *Syntroleum v. Neste* IPR2014-00192.
D. P. Duncan in "Naval Stores", D. F. Zinkel and J. Russell, Editors; Pulp Chemicals Association, New York, 1989, pp. 388-389, Exhibit 1064 in *Syntroleum v. Neste* IPR2013-00178.
D'Alonzo, R.P., et al., "Glyceride Composition of Processed Fats and Oils as Determined by Glass Capillary Gas Chromatography," JAOCS, vol. 59, No. 7, pp. 292-295 (Jul. 1982), Ex. 2040 in *Syntroleum v. Neste* IPR2013-00178.
Da Rocha Filho, G. N. et al. "Catalytic Conversion of Hevea Brasiliensis and Virola sebifera Oils to Hydrocarbon Fuels," JAOCS, vol. 69 No. 3, 266-271 (1992).
Da Rocha Filho, G. N., "Formation of alkanes, alkylcycloalkanes and alkylbenzenes during the catalytic hydrocracking of vegetable oils," Fuel 72(4) 1993, 543-549.
Davis, M. E. & Davis, R. J. Fundamentals of Chemical Reaction Engineering (McGraw-Hill, Inc., 2003), pp. 184-239, Ex. 1082 served but not filed in *Syntroleum v. Neste*—IPR 2013-00178.
Dean, J. A. (Ed.), Lange's Handbook of Chemistry, Thirteenth Edition (McGraw-Hill, Inc., 1985), pp. 7-375, 7-626 (introduced during Second Deposition of Michael T. Klein, Sc.D), Ex. 1084 served but not filed in *Syntroleum v. Neste*—IPR 2013-00178.
Decision Instituting inter partes review of U.S. Pat. No. 8,212,094 (IPR 2013-00178).
Declaration of Dr. Bruce C. Gates, Ph.D., in IPR2014-00192 for U.S. Pat. No. 8,278,492, Ex. 2001 (Aug. 18, 2014).
Declaration of Dr. Edward L. Sughure II—Inter Partes Reexamination Control No. 95/002,084 (dated Sep. 23, 2013), Ex. 2038 in *Syntroleum v. Neste*IPR2013-00178.
Declaration of Edward L. Sughrue II dated Mar. 7, 2013 in Inter Parte Review No. IPR2013-00178.
Declaration of Edward Sughrue dated Nov. 21, 2013, Exhibit 1002 in *Syntroleum v. Neste* IPR2014-00192.
Declaration of Jukka Myllyoja, Mar. 11, 2009, U.S. Pat. No. 8,022,258 File History, Exhibit 1048 in *Syntroleum v. Neste* IPR 2013-00178.
Declaration of Nelson E. Lawson (with Tab A) dated Mar. 3, 2013 in Inter Parte Review No. IPR2013-00178.
Deem, A.G. et al., "Catalytic Poisoning in Liquid-Phase Hydrogenation," Industrial and Engineering Chemistry, vol. 33, No. 11, Nov. 1941, pp. 1373-1376.
Defendant Dynamic Fuels, LLC's Fed.R.Civ.P. 7.1 Statement.
Defendants' Opening Brief in Support of Their Motion to Stay.
Defendants' Reply Brief in Support of Their Motion to Stay (Public Version).
Delmon, B., "Advances in Hydropurification Catalysts and Catalysis," Catalysts in Petroleum Refining, 1-38 (1989).
Den Otter, M. J. A. M., "The Dimerization of Oleic Acid with a Montmorillonite Catalyst I: Important Process Parameters; Some Main Reactions," Fette Seifen Anstrichmittel, vol. 72, No. 8, 1970, pp. 667-673, Ex. 1072 served but not filed in *Syntroleum v. Neste*—IPR 2013-00178.
Deposition of Michael Klein, Dec. 20, 2013 , Exhibit 1044 in *Syntroleum v. Neste* IPR2013-00178.

Deposition transcript of Dr. Edward Sughrue II, Ph.D. (Nov. 1, 2013), Neste Exhibit 2022 in *Syntroleum v. Neste* IPR2013-00178.
Deposition transcript of Dr. Nelson E. Lawson, Ph.D. (Oct. 23, 2013) (redacted), Neste Exhibit 2023 in *Syntroleum v. Neste* IPR2013-00178.
Deposition transcript of Edward L. Sughrue II, Ph.D. (Feb. 5, 2014), Ex. 2033 in *Syntroleum v. Neste* IPR2013-00178.
Deposition transcript of Nelson E. Lawson, Ph.D. (Feb. 4, 2014), Ex. 2032 in *Syntroleum v. Neste* IPR2013-00178.
Derrien, M. L. et al., "The IFP Selective Hydrogenation Process," Chemical Engineering Progress, vol. 70, No. 1, pp. 74-80 (1974).
Dwyer, J., "Zeolite structure, composition and catalysis," Chemistry and Industry, 258-269 (1984).
Dynamic Fuel's Answer, Affirmative Defenses and Counterclaims to Plaintiff's Complaint.
Edgar, M.D. et al., "Analysis is key to hydrotreater troubleshooting," Oil & Gas Journal, vol. 82, Issue 23, Jun. 4, 1984. pp. 67-70.
Elliott, D.E. et al., "Hydrodeoxygenation of Wood-Derived Liquids to Produce Hydrocarbon Fuels," Society of Automotive Engineers, Inc., 1985, pp. 1.586-1.592.
Embong et al., Sulfur content of crude rapeseed oil form aqueous extraction, 1980, JAOCS, 2 pages.
English translation of Japanese Office Action for Application No. 518886/2008 dated Dec. 21, 2010.
The Environmental Protection Agency (EPA), "Regulatory Impact Analysis: Heavy-Duty Engine and Vehicle Standards and Highway Diesel Fuel Sulfur Control Requirements," 2000 pp. iii-xix, IV-1-IV-122 (Ex. 1048 in IPR2014-00192).
EPA Method 6010C "Inductively Coupled Plasma-Atomic Emission Spectrometry" (2007), Neste Exhibit 2015 in *Syntroleum v. Neste* IPR2013-00178.
Erickson, D. R. et al., "Soybean Oil Modern Processing and Utilization," American Soybean Association, 20 pages (1990).
Excerpt from Gates, B.C., et al., Chemistry of Catalytic Processes, New York: McGraw-Hill, 1979 (Ex. 2017 in IPR2014-00192 for U.S. Pat. No. 8,278,492).
Expert Declaration of Dr. Michael T. Klein submitted in IPR2013-00178 (Nov. 11, 2013), Neste Exhibit 2019 in *Syntroleum v. Neste* IPR2013-00178.
Feng, Y. et al., "Chemical composition of tall-oil based cetane enhancer for diesel fuels," First Biomass Conference of the Americas: Energy, Environment, Agriculture, and Industry, vol. II, Aug. 30-Sep. 2, 1993, Burlington, Vermont, p. 863-875 (1993).
Ferrari, M. et al., "Influence of the hydrogen sulfide partial pressure on the hydrodeoxygenation reactions over sulfide CoMo/Carbon catalysts", Hydrotreatment and Hydrocracking of Oil Fractions, pp. 85-95 (B. Delmon et al. eds., Elsevier Science 1999) , Exhibit 1012 in *Syntroleum v. Neste* IPR2014-00192.
Ferrari, M. et al., "Influences of the Hydrogen Sulfide Partial Pressure and of a Nitrogen Compound on the Hydrodeoxygenation Activity of a CoMo/Carbon Catalyst", Journal of Catalysis 198, 47-55 (2001).
File History U.S. Appl. No. 08/269,090 to Monnier et al. (filed Jun. 30, 1994) (abandoned), Exhibit 1013 in *Syntroleum v. Neste* IPR2014-00192.
File History U.S. Appl. No. 08/517,421 to Monnier et al. (filed Aug. 21, 1995) (continuation-in-part), which issued as U.S. Pat. No. 5,705,722.
Final Decision in IPR 2013-00178 regarding U.S. Pat. No. 8,212,094 (Paper No. 63) (Aug. 29, 2014).
Formo, M. W., 31 J. Am. Oil Chemists Soc., 1954, pp. 548-559, Exhibit 1063 in *Syntroleum v. Neste* IPR2013-00178.
Forzatti, P., et al., "Catalyst Deactivation," Catalysis Today 52 (1999): 165-81 (Ex. 2008 in IPR2014-00192 for U.S. Pat. No. 8,278,492).
Froment, G. F. et al., Hydrotreatment and hydrocracking of oil fractions, 1997, Elsevier Science Ltd, $6^{th}$ European workshop, Oostende, Belgium (4 pages).
Galperin, L. B., "Hydroisomerization of N-decane in the presence of sulfur and nitrogen compounds," Applied Catalysis A: General 209 (2001) 257-268.

(56) References Cited

OTHER PUBLICATIONS

Galperin, L.B. et al., Hydroisomerization of n-decane in the presence of sulfur: Effect of metal-acid balance and metal location, Applied Catalysis A: General 219 (2001) 79-88.
Garrido, M.D., et al., "Concentrations of metals in vegetable edible oils," Food Chemistry, vol. 50, 1994, DD. 237-243.
Gelder, Elaine A. et al., "The hydrogenation of nitrogenzene to aniline: a new mechanism," Chem. Comm. 522-24 (2005) (published Dec. 2, 2004), Neste Exhibit 2029 in *Syntroleum v. Neste* IPR2013-00178.
Gellerman, M. et al., "Investigation of Spent Hydrotreating Catalysts," Translated from Khimiya i Tekhnologiya Topliv i Mase, 8, 32-34, VNII NP, Russia (1993).
Geng, C. H., Zhang, F., Gao, Z. X., Zhao, L. F., & Zhou, J. L., Hydroisomerization of n-tetradecane over Pt/SAPO-11 catalyst, Catalysis today, 93-95, 485-491 (2004).
Gislason, J., Phillips sulfur-removal process nears commercialization, Oil & Gas Journal, 2001, pp. 72-76 (Ex. 1050 in IPR2014-00192).
Goering, C.E. et al., "Fuel Properties of Eleven Vegetable Oils," American Society of Agricultural Engineers, 1982, pp. 1472-1477 and 1483.
Gopal, S. et al., Pt/H-ZSM-12 as a catalyst for the hydroisomerization of C5—C7 n-alkanes and simultaneous saturation of benzene, Applied Catalysis A: General 247 (2003) 113-123.
Gosselink, J. W. et al. "Mild Hydrocracking: Coping with Catalyst Deactivation," 34 Catalyst Deactivation 279-287 (1987).
Gregg, Donald C., *Principles of Chemistry*, pp. 244-253 (Allyn and Bacon, Inc., 2nd ed. 1963), Ex. 2044 in *Syntroleum v. Neste* IPR2013-00178.
Groschen, R. "The Feasibility of Biodiesel from Waste/Recycled Greases and Animal Fats," Marketing Services Division, Minnesota Department of Agriculture, Oct. 2002.
Gunstone, F.D. et al., The Lipid Handbook (Chapman & Hall 2d ed. 1994) pp. 47-223, 319-358, Exhibit 1006 in *Syntroleum v. Neste* IPR2014-00192.
Gusmao, et al., "Utilization of Vegetable Oils as Alternative Source for Diesel-Type Fuel," Catalysis Today, 5:533-544 (1989).
Haas, M. J., "Animal Fats", Bailey's Industrial Oil and Fat Products, Sixth Edition, vol. 1, p. 161 (2005).
Halawy S.A., "Unpromoted and $K_2O$-Promoted Cobalt Molybdate as Catalysts for the Decomposition of Acetic Acid," Monatshefte fur Chemie, vol. 134, 2003, pp. 371-380, Ex. 1075 served but not filed in *Syntroleum v. Neste*—IPR 2013-00178.
Hawley's Condensed Chemical Dictionary, $13^{th}$ Ed., 629 (1997), Neste Exhibit 2009 in *Syntroleum v. Neste* IPR2013-00178.
Hill, Jr., Charles, "*An Introduction to Chemical Engineering Kinetics & Reactor Design*," Ch. 10 Temperature and Energy Effects in Chemical Reactors, John Wiley & Sons, 1977, pp. 349-387.
Huve, L.G., "Shell Global Solutions Dewaxing Technologies & Catalysts Current Status" pp. 1-13.
Iglesia, E. et al., "Hydrogen transfer and activation of light alkanes on H-ZSM5 modified by metal cations," ACS Div. Petrol. Chem. Preprints, 38, 746-753 (1993).
Information Disclosure Citation (SB/08) filed in Control No. 90/008,899 submitted Jul. 8, 2009.
Institution Decision in IPR 2014-00192 regarding U.S. Pat. No. 8,278,492, Paper No. 18, entered Jun. 6, 2014.
Interview Summary dated Feb. 11, 2009 in U.S. Appl. No. 11/477,921.
Interview Summary dated Jan. 24, 2012 in U.S. Appl. No. 11/477,921.
Judd, B. "Biodiesel from Tallow," prepared for: Energy Efficiency and Conservation Authority (Nov. 2002).
Kasza, T., et al., "Isomerization of Paraffin Mixtures Produced from Sunflower Oil," Hungarian Journal of Industrial Chemistry, vol. 39, No. 3, pp. 363-368 (2011), Ex. 2043 in *Syntroleum v. Neste* IPR2013-00178.
Kent, James A., *Riegel's Handbook of Industrial Chemistry*, pp. 278-279 (Van Nostrand Reinhold, New York, 9th ed. 1992), Ex. 2035 in *Syntroleum v. Neste* IPR2013-00178.

Kikhtyanin, O. V., Vostrikova, L. A., Urzhuntsev, G. A., Toktarev, A. V., Tselyutina, M. I., Reznichenko, I. D., & Echevsky, G. V., Hydrotreatment of diesel feedstock over Pt-SAPO-31 catalyst: from lab to pilot scale. Studies in Surface Science and Catalysis, 174, 1227-1230 (2008).
Kirk-Othmer Encyclopedia of Chemical Technology 3rd Ed. vol. 11 pp. 682-688 (1980).
Kirk-Othmer Encyclopedia of Chemical Technology 3rd Ed. vol. 9 pp. 804-805 (1980).
Kirk-Othmer, "Dimer Acids," Encyclopedia of Chemical Technology, Third Edition, vol. 7 (John Wiley & Sons, Inc., 1984), pp. 770-771, 780, Ex. 1071 served but not filed in *Syntroleum v. Neste*—IPR 2013-00178.
Laurent, E. & Delmon, B., "Study of the Hydrodeoxygenation of Carbonyl, Carboxylic and Guaiacyl Groups over Sulfided CoMo/γ-Al2O3 and NiMo/γ-Al2O3 Catalysts. II. Influence of water, ammonia and hydrogen sulfide," 109 Applied Catalysis, 1994, pp. 97-115 ("Laurent II").
Laurent, E. & Delmon, B., "Study of the Hydrodeoxygenation of Carbonyl, Carboxylic and Guaiacyl Groups over Sulfided CoMo/γ-Al2O3 and NiMo/γ-Al2O3 Catalysts," 109 Applied Catalysis, 1994, pp. 77-96 ("Laurent I") (Ex. 1042 in IPR2013-00178).
Laurent, E. et al., "Hydrodeoxygenation of Oxygenated Model Compounds: Simulation of the Hydro-purification of Bio-oils," Adv. Thermochem Biomass Convers., Ed. Rev. pap. Int. conf., 3rd. pp. 1403-1414 (1994).
Leng, T. Y. et al., "Catalytic Conversion of Palm Oil to Fuels and Chemicals," The Canadian Journal of Chemical Engineering, vol. 77, 156(1999).
Leonard E.C., 56 J. Am. Oil Chem. Soc., 1979, pp. 782A-785A, Exhibit 1054 in *Syntroleum v. Neste* IPR2013-00178.
Leonard, E. C. (Ed.), "The Dimer Acids," Humko-Sheffield Chemical, 1975, pp. 2-3, 6-7, Ex. 1070 served but not filed in *Syntroleum v. Neste*—IPR 2013-00178.
Levenspiel, O., Chapter 9, "Temperature and Pressure Effects," *Chemical Reaction Engineering*, $3^{rd}$ ed., pp. 207-239, John Wiley & Sons.
Little, D., Catalytic Reforming, PennWell Publishing Company, 1985, pp. 220-221 (Ex. 1072 in IPR2014-00192).
Liu et al., "Production of high quality cetane enhancer from depitched tall oil," Petrol. Sci. Tech. 597 (1998) (Presented at the 1996 National AIChE Meeting, Chicago, Nov. 10-15, 1996.
Mag, T., "Canola Seed and Oil Processing," Canola Council of Canada, 1994.
Maier et al., Hydrogenolysis, IV, Chem. Ber., vol. 115, pp. 808-812 (1982).
McMurry, John, Organic Chemistry, pp. 497-500 (Brooks / Cole, 4th ed. 1996), Ex. 2037 in *Syntroleum v. Neste* IPR2013-00178.
Miller, S.J., "Studies on Wax Isomerization for Lubes and Fuels, Zeolited and Related Microporous Materials: State of the Art in 1994," Studies in Surface Science and Catalysts, 84:2319-2326 (1994).
Modhera, B. et al., Simultaneous n-hexane isomerization and benzene saturation over Pt/nano-crystalline zeolite beta, Reac. Kinet. Mech. Cat (2010) 99:421-429.
Morrison, R.T. & Boyd, R. N., Organic Chemistry, Second Edition (Allyn and Bacon, Inc., 1969), pp. 107-108, Ex. 1081 served but not filed in *Syntroleum v. Neste*—IPR 2013-00178.
Moyse, B. M., "Graded Catalyst Systems to Combat Bed-Fouling Problems," Haldor Topsoe, Inc., Houston, TX, 16 pages (1996).
Mukai, et al., "Survey of Petroleum Refining Technology for High-quality (Ultra-low Sulfur Content) Diesel Fuel", Petroleum Energy Center, 2001 (Ex. 1049 in IPR2014-00192).
Muñoz Arroyo, J.A., et al., "Hydrocracking and isomerization of n-paraffin mixtures and a hydrotreated gasoil on Pt/ZSM-22: confirmation of pore mouth and key-lock catalysis in liquid phase," Applied Catalysis A: General 192, 2000, pp. 9-22.
Nag, N.K. et al., "Characterization of Hydroprocessing Catalysts by Resolved Temperature-Programmed Desorption, Reduction, and Sulfiding", Journal of Catalysis 66, 162-170 (1980).

(56) References Cited

OTHER PUBLICATIONS

Nasirov, RK. et al., "Presulfiding of Hydrotreating Catalyst by Elemental Sulfur Outside of the Reactor," Chemistry and Technology of Fuels and Oils, vol. 34, No. 6, 1998, p. 344-348 (Ex. 1075 in IPR2014-00192).
Nawar, W.W., 17 J. Agr. Food Chem., 1969, pp. 18-21, Exhibit 1056 in *Syntroleum v. Neste* IPR2013-00178.
Neste's Mar. 17, 2008 response to an Office Action, U.S. Pat. No. 8,022,258 File History, Exhibit 1052 in *Syntroleum v. Neste* IPR2013-00178.
Neste's Oct. 19, 2009 response to an Office Action, U.S. Pat. No. 8,022,258 File History, Exhibit 1053 in *Syntroleum v. Neste* IPR2013-00178.
Nordic Business Report, M2 Communications Ltd., Mar. 9, 2005. (Ex. 1078 in IPR2014-00192).
Nunes, et al., "Soybean Oil Hydrocracking Under Pressure Process and General Aspect of the Transformation," Revue De L'institut Fransais Du Petrole, vol. 42, No. 3, May-Jun. 1986.
Office Action issued in U.S. Appl. No. 11/415,707 on Aug. 24, 2007.
Office Action mailed Nov. 18, 2008 in co-pending U.S. Appl. No. 11/477,921.
Office Action mailed Jun. 15, 2009 in co-pending U.S. Appl. No. 11/477,921.
Office Action, dated Aug. 24, 2010, for U.S. Appl. No. 11/477,921.
Office Action, dated Feb. 3, 2010, for U.S. Appl. No. 11/477,921.
Office Action, mailed Oct. 13, 2011, for U.S. Appl. No. 11/477,921.
Ooi, T. L. et al., "Reaction of Palm Stearin Catalyzed by Ni(II) Ion-Exchanged Zeolite 13X," Yukagaku,, 35(5), 354-358, Palm Oil Res. Inst., Kuala Lumpur, Malaysia (1986).
Parker, Sybil P., *McGraw-Hill Dictionary of Scientific and Technical Terms*, p. 439 (5th ed. 1994), Ex. 2042 in *Syntroleum v. Neste* IPR2013-00178.
Paschke, R. F et al., 41 J. Am. Oil Chem. Soc., 1964, pp. 723-727, Exhibit 1055 in *Syntroleum v. Neste* IPR2013-00178.
Paschke, R.F. et al., 26 J. Am. Oil Chemists Soc., 1949, pp. 278-283, Exhibit 1062 in *Syntroleum v. Neste* IPR2013-00178.
Patent Owner's Contingent Motion to Amend in IPR 2014-00192 filed Aug. 18, 2014 (Paper No. 25).
Patent Owner Oral Hearing Demonstrative, Exhibit 2045 in *Syntroleum v. Neste*—IPR 2013-00178.
Patent Owner's Motion to Amend Claims in IPR 2013-00178 (Nov. 11, 2013).
Patent Owner's Reply to Petitioner's Opposition to Patent Owner's Motion to Amend, dated Feb. 11, 2014 in *Syntroleum v. Neste* IPR2013-00178.
Patent Owner's Preliminary Response submitted in *Syntroleum v. Neste* IPR2013-00178 (Paper No. 11) (Jun. 14, 2013).
Patent Owner's Response filed Aug. 18, 2014 in IPR 2014-00192 (Paper No. 26).
Patent Owner's Reply to Petitioner's Motion for Observations in IPR2013-00178 (Paper No. 56) (Mar. 14, 2014).
Patnaik, P., Handbook of Organic Chemicals, the McGraw-Hill Companies, Inc., 2003, pp. 186-187 (Ex. 1071 in IPR2014-00192).
Pearl, G., "Animal Fats and Recycled Cooking Oils: Alternatives as Burner Fuels," Fats and Proteins Research Foundation, http://fatforfuel.us/images/GaryPearl.pdf, Mar. 2001.
Petition for Inter Partes Review of U.S. Pat. No. 8,278,492 (2013) (IPR 2014-00192).
Petition for Inter Partes Review of U.S. Pat. No. 8,212,094 dated Mar. 8, 2013 in Inter Parte Review No. IPR2013-00178.
Petitioner's Opposition to Patent Owner's Motion to Amend dated Jan. 13, 2014 in *Syntroleum v. Neste* IPR2013-00178.
Petitioner's Opposition to Patent Owner's Motion to Amend filed Nov. 3, 2014 in IPR 2014-00192 of U.S. Pat. No. 8,212,094 (Paper No. 30).
Petitioner's Reply to Patent Owner's Response filed Nov. 3, 2014 in IPR 2014-00192 of U.S. Pat. No. 8,212,094 (Paper No. 31).
Petrocelli, F. P. et al., 5 Fuel Sci. & Tech., 1987, pp. 25-62, Exhibit 1045 in *Syntroleum v. Neste* IPR2013-00178.

Plantenga, F. L., et al., ""Nebula": A Hydroprocessing Catalyst with Breakthrough Activity," Stud. Surf. Sci. Catal. vol. 145, 2003, pp. 407-410; http://dx.doi.org/10.1016/S0167-2991(03)80246, Ex. 1078 served but not filed in *Syntroleum v. Neste*—IPR 2013-00178.
Prakash, Dr. C. B., "A Critical Review of Biodiesel as a transportation fuel in Canada," GCSI—Global Change Strategies International Inc. (1998).
Prosecution History of Raulo (U.S. Pat. No. 6,399,845 B1) (Ex. 1062 in IPR2014-00192).
U.S. Appl. No. 60/695,853, filed Jul. 5, 2005, Neste Exhibit 2018 in *Syntroleum v. Neste* IPR2013-00178.
U.S. Appl. No. 60/695,852, filed Jul. 5, 2005 (Ex. 2004 in IPR2014-00192 for U.S. Pat. No. 8,278,492).
Przybylski, R., "Canola Oil: Physical and Chemical Properties," Canola Council of Canada; no date provided.
Antoniassi, R. et al., "Pretreatment of Corn Oil for Physical Refining," *JAOCS*, vol. 75, No. 10, 1998, pp. 1411-1415.
Raed H. Abudawood, Faisal M. Alotaibi, and Arthur A. Garforth, Hydroisomerization of n-Heptane over Pt-Loaded USY Zeolites. Effect of Steaming, Dealumination, and the Resulting Structure on Catalytic Properties, Ind. Eng. Chem. Res. 2011, 50, 9918-9924 (2011).
Rantanen, L., et al., "NExBTL—Biodiesel Fuel of the Second Generation" SAE Technical Paper 2005-01-3771 (published Oct. 24, 2005).
Record of Oral Hearing in IPR2013-00178 (Paper No. 60) (Apr. 30, 2014).
Reel/Frame 010719/0026, change of name recorded Apr. 3, 2000 (Ex. 1076 in IPR2014-00192).
Reel/Frame 022177/0623, assignment recorded Feb. 2, 2009 (Ex. 1077 in IPR2014-00192).
Response to Communication Pursuant to Article 96(2) EPC, May 31, 2005 in European Patent Application No. 03396079.0 (Ex. 1053 in IPR2014-00192).
Ribamar et al., "Vegetable Oil Catalytic Breakdown," Petrobras Technical Bulletin, Rio de Janeiro, 24 (2): 130-147, Apr./Jun. 1981.
Ribamar et al. "Catalytic Decomposition of Vegetable Oil," Applied Catalysis, vol. 5., 1983, pp. 299-308.
Robinson, J. M., et al., "Chemical Conversion of Biomass Polysaccharides to Liquid Hydrocarbon Fuels and Chemicals", Preprints of Symposia—Division of Fuel Chemistry American Chemical Society; 44, 2; 224-227 (2000).
Romero, M; Perot, G; Gueguen, C; Guisnet, M; Improvement by Sulfur of the Hydroisomerization Selectivity of Platinum-Mordenite Catalysts; Applied Catalysis, vol. 1, Issue: 5, pp. 273-275 (1981).
Sanford, E. et al., "Improved Catalyst Loading Reduces Guard Reactor Fouling," Oil & Gas Journal, Dec. 19, 1988, pp. 35-41.
Satterfield, C.N., Heterogeneous Catalysis In Industrial Practice, 2nd Edition, McGraw-Hill, Inc., NY (1991), pp. 375-389.
Schmidt et al., Society of Automotive Engineers, Inc., pp. 113-123 (1996).
Schuit, G.C.A., "Chemistry and Engineering of Catalytic Hydrodesulfurization," AIChE Journal, vol. 19, No. 3, May 1973, pp. 417-438 (Ex. 1074 in IPR2014-00192).
Second Declaration of Dr. Michael T. Klein, dated Feb. 11, 2014, Ex. 2041 in *Syntroleum v. Neste* IPR2013-00178.
Second Declaration of Edward Sughrue, dated Jan. 13, 2014, Exhibit 1040 in *Syntroleum v. Neste* IPR2013-00178.
Second Declaration of Edward Sughrue dated Nov. 3, 2014 in IPR2014-00192 (Ex. 1043).
Second Declaration of Nelson Lawson, dated Jan. 12, 2014, Exhibit 1041 in *Syntroleum v. Neste* IPR2013-00178.
Second Deposition transcript of Dr. Klein Sc.D., Feb. 18, 2014, Exhibit 1088 in *Syntroleum v. Neste*—IPR2013-00178.
Senol et al., 100 Catal. Today, 2005, pp. 331-335, Exhibit 1046 in *Syntroleum v. Neste* IPR2013-00178.
Senol, O. I. et al., "Hydrodeoxygenation of aliphatic esters on sulphided NiMo/γ-Al2O3 and CoMo/γ-Al2O3 catalyst: The effect of water," Catalysis Today 106, pp. 186-189 (Aug. 2005).
Sharma, R. K., et al., "Conversion of fatty acids and esters to low-aromatic gasoline," American Chemical Society, Division of Fuel Chemistry 1994 34(4) 1040-1042.

(56) References Cited

OTHER PUBLICATIONS

Sharp, D.W.A. (Ed.), The Penguin Dictionary of Chemistry, $2^{nd}$ Edition, Penguin Books, 1990, pp. 207, 263, 432, 433.
Smith, M.B. et al., March's Advanced Organic Chemistry—Reactions, Mechanisms, and Structure, Fifth Edition, John Wiley & Sons, Inc., 2001, pp. 808-811 (Ex. 1046 in IPR2014-00192).
Snape, C. et al., "The Chemical Nature of Asphaltenes From Some Coal Liquefaction Processes", Fuel Processing Technology 8, 155-168 (1984).
Solomons, T.W. Graham, *Organic Chemistry*, pp. 392-394 (John Wiley and Sons, 1980), Ex. 2036 in *Syntroleum v. Neste* IPR2013-00178.
Song, C. et al., "Mesoporous molecular sieve MCM-41 supported Co—Mo catalyst for hydrodesulfurization of dibenzothiophene in distillate fuels," Applied Catalysis A: General 176, pp. 1-10 (1999).
Soveran, D.W. et al., "The Effect on Diesel Engine Emissions with High Cetane Additives from Biomass Oils," (1992).
Spataru, A. et al. "AGTANE (AGricultural ceTANE): An economically viable bioenergy product for compression ignited engines," The Adept Group, Inc., CANMET Energy Technology Centre (2001).
Specification, Abstract, Claims and Drawings as filed in U.S. Appl. No. 13/107,146, filed May 13, 2011, Neste Exhibit 2017 in *Syntroleum v. Neste* IPR2013-00178.
Stork, W.H.J., "Molecules, catalysts, and reactors in hydroprocessing of oil fractions," Hydrotreatment and Hydrocracking of Oil Fractions, 41 (1997).
Stumborg, M., et al., "Catalytic Conversion of Vegetable Oils to Diesel Additives", Energy From Biomass and Wastes XVI, Institute of Gas Technology (1993).
Stumborg, M., et al., "Hydroprocessed Vegetable Oils for Diesel Fuel Improvement," Liquid Fuels, Lubricants and Additives from Biomass, Proceedings of an Alternative Energy Conference (1994).
Supplement to Second Declaration of Dr. Edward Sughrue, Ex. 1077 served but not filed in *Syntroleum v. Neste*—IPR 2013-00178.
Supplement to Second Declaration of Dr. Nelson Lawson, Exhibit 1069, served but not filed in *Syntroleum v. Neste*—IPR 2013-00178.
Syntroleum Corporation Form 10-K dated Aug. 14, 2014, http://www.sec.gov/Archives/edgar/data/1029023/000119312514097644/d690055d10k.htm (Ex. 2016 in IPR2014-00192 for U.S. Pat. No. 8,278,492).
Syntroleum Corporation Form 10-Q filed Aug. 8, 2012 for the Period Ending Jun. 30, 2012.
Syntroleum Oral Hearing Demonstrative, Exhibit 1089 in *Syntroleum v. Neste*—IPR 2013-00178.
Syntroleum's Answer, Affirmative Defenses and Counterclaims to Plaintiff's Complaint.
Tanaka, Y. et al., "A Practical Approach to 10 ppm Sulfur Diesel Production,", Proceedings of 13th Saudi-Japanese Catalyst Symposium, Dhahran, Saudi Arabia (Dec. 2003).
TOFA Laboratory Report, Summit Environmental Technologies, issued Feb. 27, 2013.
Transcript of Deposition of Bruce C. Gates, Ph.D., taken Oct. 17, 2014 in IPR2014-00192 of U.S. Pat. No. 8,212,094 (Ex. 1065).
Twaiq, F. A. et al., "Catalytic Conversion of Palm Oil to Hydrocarbons: Performance of Various Zeolite Catalysts," Ind. Eng. Chem. Res. 38, pp. 3230-3237 (1999).
Tyson, K. et al., "Biomass Oil Analysis: Research Needs and Recommendations" Technical Report, National Renewable Energy Laboratory, Colorado (2004).
Tyson's Answer, Affirmative Defenses and Counterclaims to Plaintiff's Complaint.
U.S. Pat. No. 8,187,344, U.S. Order Granting Request for Inter Partes Reexam, and Inter Partes Reexamination Communication. Sep. 14, 2012 in Reexamination No. 95/002,084.
U.S. Appl. No. 11/477,921, filed Jun. 30, 2006 (Ex. 2003 in IPR2014-00192 for U.S. Pat. No. 8,278,492).
Vegetable Oils in Food Technology: Composition, Properties and Uses (Gunstone, Ed., 2002).

Venkatachalam et al., 22 J. Poly. Sci. Poly. Chem. Ed., 1984, pp. 3805-3814, Exhibit 1051 in *Syntroleum v. Neste* IPR2013-00178.
Vollhardt, K.P.C. & Schore, N.E., Organic Chemistry: Structure and Function, Third Edition, (W.H. Freeman and Company, New York, NY, 2000), p. 57, Ex. 1080 served but not filed in *Syntroleum v. Neste*—IPR 2013-00178.
Wang, T. et al., Sulfur on Noble Metal Catalyst Particles. Journal of Catalysis, 78(2), 306-318 (1982).
Wang, X. et al., "Studies on nickel-based binetallic catalysts for hydrodeoxygenation," Ranliao Huaxue Xuebao, 33 Journal of Fuel Chemistry and Technology (5), 612-616 (Oct. 2005).
Wong, A. et al. "Conversion of Vegetable Oils and Animal Fats into Paraffinic Cetane Enhancers for Diesel Fuels," Second Biomass Conference of the Americas (1995).
Wong, A., "Tall Oil Based Cetane Enhancer for Diesel Fuel," $79^{th}$ Annual Meeting Technical Section, Canadian Pulp and Paper Association (1993).
Wong, A., "Technical and Economic Aspects of Manufacturing Cetane-Enhanced Diesel Fuel" from Canola Oil, Bio-Oils Symposium Saskatoon, Saskatchewan (1994).
Written Submission and Amendments in Response to Summons to Attend Oral Proceedings Pursuant to Rule 71(1) EPC, Jan. 20, 2006 in European Patent Application No. 03396079.0 (Ex. 1052 in IPR2014-00192).
York, Andrew P.E. et al., Comparative Effect of Organosulfur Compounds on Catalysts for the n-Heptane Isomerization Reaction at Medium Pressure: $Mo_2C$-Oxygen-Modified, $MoO_3$-Carbon-Modified, Pt γ/-Al2O3, and Pt/ β-Zeolite Catalysts, Ind. Eng. Chem. Res. 1996, 35, 672-682.
Yu, G.X. et al., RE2O3-promoted Pt—SO4 2-/ZrO2—Al2O3 catalyst in n-hexane hydroisomerization, Catalysis Today 166 (2011) 84-90.
Reply to Petitioner's Opposition to Patent Owner's Motion to Amend (Paper No. 34 in IPR 2014-00192).
Bartholomew, H. and R. J. Farrauto, Fundamentals of Industrial Catalytic Processes, Chapman & Hall (1st ed. 1997) (Ex. 2026 in IPR 2014-00192).
Bartholomew, H. and R. J. Farrauto, Fundamentals of Industrial Catalytic Processes, John Wiley & Sons (2nd ed. 2006)(Ex. 2027 in IPR 2014-00192).
Weisser and Landa, Metal Sulphide Catalysts, their Properties and Applications, Academia (1972) ((Ex. 2028 in IPR 2014-00192)).
Speight, J.G. The Chemistry and Technology of Petroleum, Marcel Dekker, New York (2nd ed. 1991) (Ex. 2029 in IPR 2014-00192).
Speight, J.G. The Chemistry and Technology of Petroleum, CRC Press (4th ed. 2007) (Ex. 2030 in IPR 2014-00192).
Girgis, M.J. and B. C. Gates, "Reactivities, Reaction Networks, and Kinetics in High-Pressure Catalytic Hydroprocessing," *I&EC Research*, 30 (1991): 2021-2058 (Ex. 2031 in IPR 2014-00192).
Second Declaration of Dr. Bruce C. Gates (Ex. 2032 in IPR 2014-00192).
Edible Canola Lab Analysis Report (Ex. 1005 in IPR2013-00178).
Deposition Transcript of Dr. Edward Lawrence Sughrue, II (Nov. 25, 2014) (Ex. 2033 in IPR 2014-00192).
Deposition Transcript of Dr. Bruce C. Gates on Jan. 8, 2015 (Ex. 1079 in 2014-00192).
Brief For Appellant-Patent Owner Neste Oil Oyj; 2015-1075 (Federal Circuit Appeal of IPR2013-00178) (Jan. 21, 2015).
Motion for Observations on Deposition of Dr. Gates (IPR2014-00192) (Jan. 14, 2015).
Response to Motion for Observations on Deposition of Dr. Gates (IPR2014-00192) (Jan. 23, 2015).
Brief for Appellee REG Synthetic Fuels, LLC; Case No. 2015-1075 (Federal Circuit Appeal of IPR2013-00178) (Mar. 6, 2015).
Reply Brief for Appellant Patent Owner Neste Oil Oyj ; Case No. 2015-1075 (Federal Circuit Appeal of IPR2013-00178) (Mar. 23, 2015).
Record of Oral Hearing in IPR2014-00192—Mar. 10, 2015.
Judgment in Appeal of IPR 2013-00178, Case No. 2015-1075 (Jun. 8, 2015).
*REG Synthetic Fuels, LLC v. Neste Oil Oyj*, IPR 2014-00192 (Final Decision regarding U.S. Pat. No. 8,278,492) (Paper No. 48) (Jun. 5, 2015).

(56) References Cited

OTHER PUBLICATIONS

Petition, Paper No. 2 in *REG Synthetic Fuels v. Neste* IPR2018-01375.
Declaration of Edward Sughrue dated Jul. 31, 2018, Exhibit 1002 in *REG Synthetic Fuels v. Neste* IPR2018-01375.
Curriculum Vitae of Edward Sughrue, Exhibit 1003 in *REG Synthetic Fuels v. Neste* IPR2018-01375.
Furimsky, E., "Catalytic Hydrodeoxygenation," Applied Catalysis A: General 199 (2000) 147-190.
Marangozis, J., "Rate and Mechanism of Hydrogenation of Cottonseed Oil in Slurry Reactors," Ind. Eng. Chem., Process Des. Dev., vol. 16, No. 3 (1977).
Prehydrogenation, Hydrodeoxygenation and Countercurrent Isomerization of Rapeseed Oil (undated).
Antoniassi, R. et al., "Pretreatment of Corn Oil for Physical Refining," *JAOCS*, vol. 75, No. 10, 1998, pp. 1411-1415, Exhibit 1032 in *REG Synthetic Fuels v. Neste* IPR2018-01375.
Sharp, D.W.A. (Ed.), The Penguin Dictionary of Chemistry, $2^{nd}$ Edition, Penguin Books, 1990, pp. 207, 263, 432, 433, Exhibit 1004 in *REG Synthetic Fuels v. Neste* IPR2018-01375.
Viljava, T., *From Biomass to Fuels: Hydrotreating of Oxygen-Containing Feeds on a CoMo/$Al_2O_3$ Hydrodesulfurization Catalyst* (2001).
Excerpts from the file history of U.S. Appl. No. 13/491,182 (now U.S. Pat. No. 8,859,832), Exhibit 2001 in Inter Partes Review No. 2018-01375.
Declaration of Michael T. Klein, Sc.D., dated May 20, 2019, Exhibit 2002 in Inter Partes Review No. 2018-01375.
Patent Owner's Response, dated May 20, 2019, Paper No. 17 in Inter Partes Review No. 2018-01375.
Patent Owner's Contingent Motion to Amend, dated May 20, 2019, Paper No. 19 in Inter Partes Review No. 2018-01375.
Final Written Decision, dated Feb. 18, 2020, Paper No. 36 in Inter Partes Review No. 2018-01375.

\* cited by examiner

PROCESS FOR THE MANUFACTURE OF DIESEL RANGE HYDROCARBONS

CROSS REFERENCE TO RELATED APPLICATIONS

This application is a Continuation of application Ser. No. 17/015,639, filed on Sep. 9, 2020. application Ser. No. 17/015,639 is a Continuation of application Ser. No. 16/715,871, filed on Dec. 16, 2019, now U.S. Pat. No. 10,800,976. application No. 16,715,871 is a Continuation of application Ser. No. 16/039,210, filed on Jul. 18, 2018, now U.S. Pat. No. 10,550,332, with an issue date of Feb. 4, 2020. application Ser. No. 16/039,210 is a Continuation of application Ser. No. 15/428,080, filed on Feb. 8, 2017, now U.S. Pat. No. 10,059,887, with an issue date of Aug. 28, 2018. application Ser. No. 15/428,080 is a Continuation of application Ser. No. 14/477,758, filed on Sep. 4, 2014, now U.S. Pat. No. 9,598,327, with an issue date of Mar. 21, 2017. application Ser. No. 14/477,758 is a Continuation of application Ser. No. 13/491,182, filed on Jun. 7, 2012, now U.S. Pat. No. 8,859,832, with an issue date of Oct. 14, 2014. application Ser. No. 13/491,182 is a Continuation of application Ser. No. 13/107,146, filed on May 13, 2011, now U.S. Pat. No. 8,212,094, with an issue date of Jul. 3, 2012. application Ser. No. 13/107,146 is a Divisional of application Ser. No. 11/477,922 filed on Jun. 30, 2006, now U.S. Pat. No. 8,022,258, with an issue date of Sep. 20, 2011, which claims the benefit of U.S. Provisional Application No. 60/695,853 filed on Jul. 5, 2005. The entire contents of all of the above applications are is hereby incorporated by reference.

FIELD OF THE INVENTION

The invention relates to an improved process for the manufacture of hydrocarbons, particularly diesel range hydrocarbons from bio oils and fats, wherein the formation of higher molecular weight compounds is reduced. The invention also relates to processing of feedstock containing free fatty acids, using a high product recycle/fresh oil-ratio at reduced reaction temperatures.

BACKGROUND OF THE INVENTION

Environmental interests and an increasing demand for diesel fuel, especially in Europe, encourage fuel producers to employ more intensively available renewable sources. In the manufacture of diesel fuels based on biological raw materials, the main interest has concentrated on vegetable oils and animal fats comprising triglycerides of fatty acids. Long, straight and mostly saturated hydrocarbon chains of fatty acids correspond chemically to the hydrocarbons present in diesel fuels. However, neat vegetable oils display inferior properties, particularly extreme viscosity and poor stability and therefore their use in transportation fuels is limited.

Conventional approaches for converting vegetable oils or other fatty acid derivatives into liquid fuels comprise trans-esterification, catalytic hydrotreatment, hydrocracking, catalytic cracking without hydrogen and thermal cracking among others. Typically triglycerides, forming the main component in vegetable oils, are converted into the corresponding esters by the transesterification reaction with an alcohol in the presence of catalysts. The obtained product is fatty acid alkyl ester, most commonly fatty acid methyl ester (FAME). Poor low-temperature properties of FAME however limit its wider use in regions with colder climatic conditions. Said properties are the result of the straight chain nature of the FAME molecule and thus double bonds are needed in order to create even bearable cold flow properties. Carbon-carbon double bonds and ester groups however decrease the stability of fatty acid esters, which is a major disadvantage of transesterification technology. Further, Schmidt, K., Gerpen J. V.: SAE paper 961086 teaches that the presence of oxygen in esters results in undesirable higher emissions of $NO_x$, in comparison to conventional diesel fuels.

Undesired oxygen may be removed from fatty acids or their esters by deoxygenation reactions. The deoxygenation of bio oils and fats, which are oils and fats based on biological material, to produce hydrocarbons suitable as diesel fuel products, may be carried out by catalytic hydroprocessing, such as hydrocracking, but also more controlled hydrotreating conditions may be utilized.

During hydrotreating, particularly hydrodeoxygenation oxygen containing groups are reacted with hydrogen and removed through formation of water and therefore this reaction requires rather high amounts of hydrogen. Due to the highly exothermic nature of these reactions, the control of reaction heat is extremely important. Impure plant oil/fat or animal fat/oil, high reaction temperatures, insufficient control of reaction temperature or low hydrogen availability in the feed stream may cause unwanted side reactions, such as cracking, polymerisation, ketonisation, cyclisation and aromatisation, and coking of the catalyst. These side reactions also decrease the yield and the properties of diesel fraction obtained.

Unsaturated feeds and free fatty acids in bio oils and fats may also promote the formation of heavy molecular weight compounds, which may cause plugging of the preheating section and decrease catalyst activity and life.

The fatty acid composition, size and saturation degree of the fatty acid may vary considerably in feedstock of different origin. The melting point of bio oil or fat is mainly a consequence of saturation degree. Fats are more saturated than liquid oils and in this respect need less hydrogen for hydrogenation of double bonds. Double bonds in a fatty acid chain also promote different kinds of side reactions, such as oligomerisation/polymerization, cyclisation/aromatisation and cracking reactions, which deactivate catalyst, increase hydrogen consumption and reduce diesel yield.

Plant oils/fats and animal oils/fat may contain typically 0-30% of free fatty acids, which are formed during enzymatic hydrolysis of triglycerides especially when oil seeds are kept in humid atmosphere. Free fatty acids can be also formed during purification of bio oils and fats, especially during caustic wash i.e. alkali catalyzed hydrolysis. The amount of free fatty acids present in plant/vegetable oils is typically 1-5 wt % and in animal fat 10-25 wt-%. Free fatty acids are corrosive in their nature, they can attack against materials of unit or catalyst and can promote some side reactions. Free fatty acids react very efficiently with metal impurities producing metal carboxylates, which promote side reaction chemistry.

Fatty acids may also promote the formation of heavy compounds. The boiling range of these heavy compounds is different from the range of diesel fuel and may shorten the life of isomerisation catalyst. Due to the free fatty acids contained in bio oils and fats, the formation of heavy molecular weight compounds are significantly increased compared to triglyceridic bio feeds, which have only low amount of free fatty acids (<1%).

Biological raw materials often contain metal compounds, organic nitrogen, sulphur and phosphorus compounds, which are known catalyst inhibitors and poisons inevitably reducing the service life of the catalyst and necessitating more frequent catalyst regeneration or change. Metals in bio oils/fats inevitably build up on catalyst surface and change the activity and selectivity of the catalyst. Metals can promote some side reactions, but blocking of catalyst active sites typically decreases the activity and thus metal impurities such as Na, Ca, and Mg compounds should be removed as efficiently as possible.

Hydrolysis of triglycerides produces also diglycerides and monoglycerides, which are partially hydrolyzed products. Diglycerides and monoglycerides are surface-active compounds, which can form emulsions and make liquid/liquid separations of water and oil more difficult. Bio oils and fats can also contain other glyceride-like surface-active impurities like phospholipids (for example lecithin), which have phosphorus in their structures. Phospholipids are gum like materials, which can be harmful for catalysts. Natural oils and fats also contain other types of components, such as waxes, sterols, tocopherols and carotenoids, some metals and organic sulphur compounds as well as organic nitrogen compounds. These compounds can be harmful for catalysts or pose other problems in processing.

U.S. Pat. Nos. 4,992,605, 5,705,722 describe processes for the production of diesel fuel additives by conversion of bio oils into saturated hydrocarbons under hydroprocessing conditions with CoMo and NiMo catalysts. The process operates at high temperatures of 350-450° C. and produces n-paraffins and other hydrocarbons. The product has a high cetane number but poor cold properties (melting point >20° C.), which limits the amount of product that can be blended in conventional diesel fuels in summer time and prevent its use during winter time. The formation of heavy compounds with a boiling point above 343° C. was observed, especially when a fatty acid fraction was used as a feed. A reaction temperature with a lower limit of 350° C. was concluded as a requirement for trouble-free operation.

A two-step process is disclosed in FI 100248, for producing middle distillates from vegetable oil by hydrogenating fatty acids or triglycerides of vegetable oil origin using commercial sulphur removal catalysts, such as NiMo and CoMo, to give n-paraffins, followed by isomerising said n-paraffins using metal containing molecular sieves or zeolites to obtain branched-chain paraffins. The hydrotreating was carried out at rather high reaction temperatures of 330-450° C., preferably 390° C. Hydrogenating fatty acids at those high temperatures leads to shortened catalyst life resulting from coking and formation of side products.

EP 1 396 531 describes a process containing at least two steps, the first one being a hydrodeoxygenation step and the second one being a hydroisomerisation step utilizing counter-current flow principle, and using biological raw material containing fatty acids and/or fatty acid esters as the feedstock. The process comprises an optional stripping step.

Deoxygenation of plant oils/fats and animal fats with hydrogen use a large amount of hydrogen and at the same time releases significant amount of heat. Heat is produced from deoxygenation reactions and from double bond hydrogenation. Different feedstocks produce significantly different amounts of reaction heat. The variation of reaction heat produced is mainly dependent on double bond hydrogenation. The average amount of double bonds per triglyceride molecule can vary from about 1.5 to more than 5 depending on the source of bio oil or fat.

FR 2,607,803 describes a process for hydrocracking of vegetable oils or their fatty acid derivatives under pressure to give hydrocarbons and to some extent acid. The catalyst contains a metal dispersed on a support. A high temperature of 370° C. did not result complete oxygen removal or high selectivity of n-paraffins. The product mixture formed, contained also some intermediate fatty acid compounds.

Formation of water during hydrotreatment results from the deoxygenation of triglyceride oxygen by the means of hydrogen (hydrodeoxygenation). Deoxygenation under hydrodeoxygenation conditions is to some extent accompanied by a decarboxylation reaction pathway and a decarbonylation reaction pathway. Deoxygenation of fatty acid derivatives by decarboxylation and/or decarbonylation reactions forms carbon oxides ($CO_2$ and CO) and aliphatic hydrocarbon chains with one carbon atom less than in the original fatty acid molecule. Decarb-reactions mean here decarboxylation and/or decarbonylation reactions.

The feasibility of decarboxylation varies greatly with the type of carboxylic acid or derivative thereof used as the starting material. Alpha-hydroxy, alpha-carbonyl and dicarboxylic acids are activated forms and thus they are more easily deoxygenated by decarb-reactions. Saturated aliphatic acids are not activated this way and generally are difficult to deoxygenate through decarb-reactions.

Decarboxylation of carboxylic acids to hydrocarbons by contacting carboxylic acids with heterogeneous catalysts was suggested by Maier, W. F. et al: Chemische Berichte (1982), 115(2), 808-12. Maier et al tested $Ni/Al_2O_3$ and $Pd/SiO_2$ catalysts for decarboxylation of several carboxylic acids. During the reaction the vapors of the reactant were passed through a catalytic bed together with hydrogen. Hexane represented the main product of the decarboxylation of the tested compound heptanoic acid. When nitrogen was used instead of hydrogen no decarboxylation was observed.

U.S. Pat. No. 4,554,397 discloses a process for the manufacture of linear olefins from saturated fatty acids or esters, suggesting a catalytic system consisting of nickel and at least one metal selected from the group consisting of lead, tin and germanium. With other catalysts, such as Pd/C, low catalytic activity and cracking to saturated hydrocarbons, or formation of ketones when Raney-Ni was used, were observed.

OBJECT OF THE INVENTION

An object of the invention is an improved process for the manufacture of diesel range hydrocarbons from bio oils and fats, with high selectivity, essentially without side reactions and with high diesel yield.

A further object of the invention is an improved process for the manufacture of diesel range hydrocarbons from bio oils and fats, wherein the extent of high molecular weight compounds formed during hydrotreating is decreased and the stability of the catalyst is increased.

A still further object of the invention is an improved process for the manufacture of diesel range hydrocarbons from bio oils and fats, wherein the hydrotreatment of triglyceride feedstock containing free fatty acids is carried out using dilution of fresh feed and reduced reaction temperature.

A still further object of the invention is an improved process for the manufacture of diesel range hydrocarbons from bio oils and fats, which process produces high quality diesel component with high yield.

Characteristic features of the process according to the invention are provided in the claims.

Definitions

Here hydroprocessing is understood as catalytic processing of organic material by all means of molecular hydrogen.

Here hydrotreatment is understood as a catalytic process, which removes oxygen from organic oxygen compounds as water (hydrodeoxygenation, HDO), sulphur from organic sulphur compounds as dihydrogen sulphide ($H_2S$) (hydrodesulphurisation, HDS), nitrogen from organic nitrogen compounds as ammonia ($NH_3$) (hydrodenitrogenation, HDN) and halogens, for example chlorine from organic chloride compounds as hydrochloric acid (HCl) (hydrodechlorination, HDCl), typically under the influence of sulphided NiMo or sulphided CoMo catalysts.

Here deoxygenation is understood to mean removal of oxygen from organic molecules, such as fatty acid derivatives, alcohols, ketones, aldehydes or ethers by any means previously described.

Here hydrodeoxygenation (HDO) of triglycerides or other fatty acid derivatives or fatty acids is understood to mean the removal of carboxyl oxygen as water by the means of molecular hydrogen under the influence of catalyst.

Here decarboxylation and/or decarbonylation of triglycerides or other fatty acid derivatives or fatty acids is understood to mean removal of carboxyl oxygen as $CO_2$ (decarboxylation) or as CO (decarbonylation) with or without the influence of molecular hydrogen. Decarboxylation and decarbonylation reactions either together or alone are referred to as decarb-reactions.

Here hydrocracking is understood as catalytic decomposition of organic hydrocarbon materials using molecular hydrogen at high pressures.

Here hydrogenation means saturation of carbon-carbon double bonds by means of molecular hydrogen under the influence of a catalyst.

Here n-paraffins mean normal alkanes or linear alkanes that do not contain side chains.

Here isoparaffins mean alkanes having one or more $C_1$-$C_9$, typically $C_1$-$C_2$ alkyl side chains, typically mono-, di-, tri- or tetramethylalkanes.

The feed (total feed) to the hydotreating unit is here understood to comprise fresh feed and at least one dilution agent.

SUMMARY OF THE INVENTION

The present invention relates to an improved process for the manufacture of hydrocarbons from renewable sources, such as plant oils/fats and animal oils/fats, comprising a hydrotreating step and an isomerisation step. Particularly the invention relates to the transformation of the starting materials comprising triglycerides, fatty acids and derivatives of fatty acids or combinations of thereof, into n-paraffins with reduced formation of high molecular weight hydrocarbons using dilution of fresh feed and reduced reaction temperature in the hydrotreating step and converting the obtained n-paraffins into diesel range branched alkanes using isomerisation, with high diesel yield. The hydrotreating step is carried out contacting the feed comprising fresh feed and at least one diluting agent with a hydrotreatment catalyst under hydrotreatment conditions. Then the obtained product is isomerised with an isomerisation catalyst under isomerisation conditions. The hydrocarbon oil formed via this process is a high quality diesel component.

DETAILED DESCRIPTION OF THE INVENTION

It was surprisingly found that dilution of fresh feed in the hydrotreatment step, in combination with decreased reaction temperature reduces the undesired side reactions and improves reaction selectivity, particularly when a starting material containing free fatty acids is used. The diluting agent can be a hydrocarbon of biological origin and/or non-biological origin. The dilution agent can also be recycled product from the process (product recycle). The diluting agent/fresh feed-ratio is 5-30:1, preferably 10-30:1 and most preferably 12-25:1.

Figure 1:
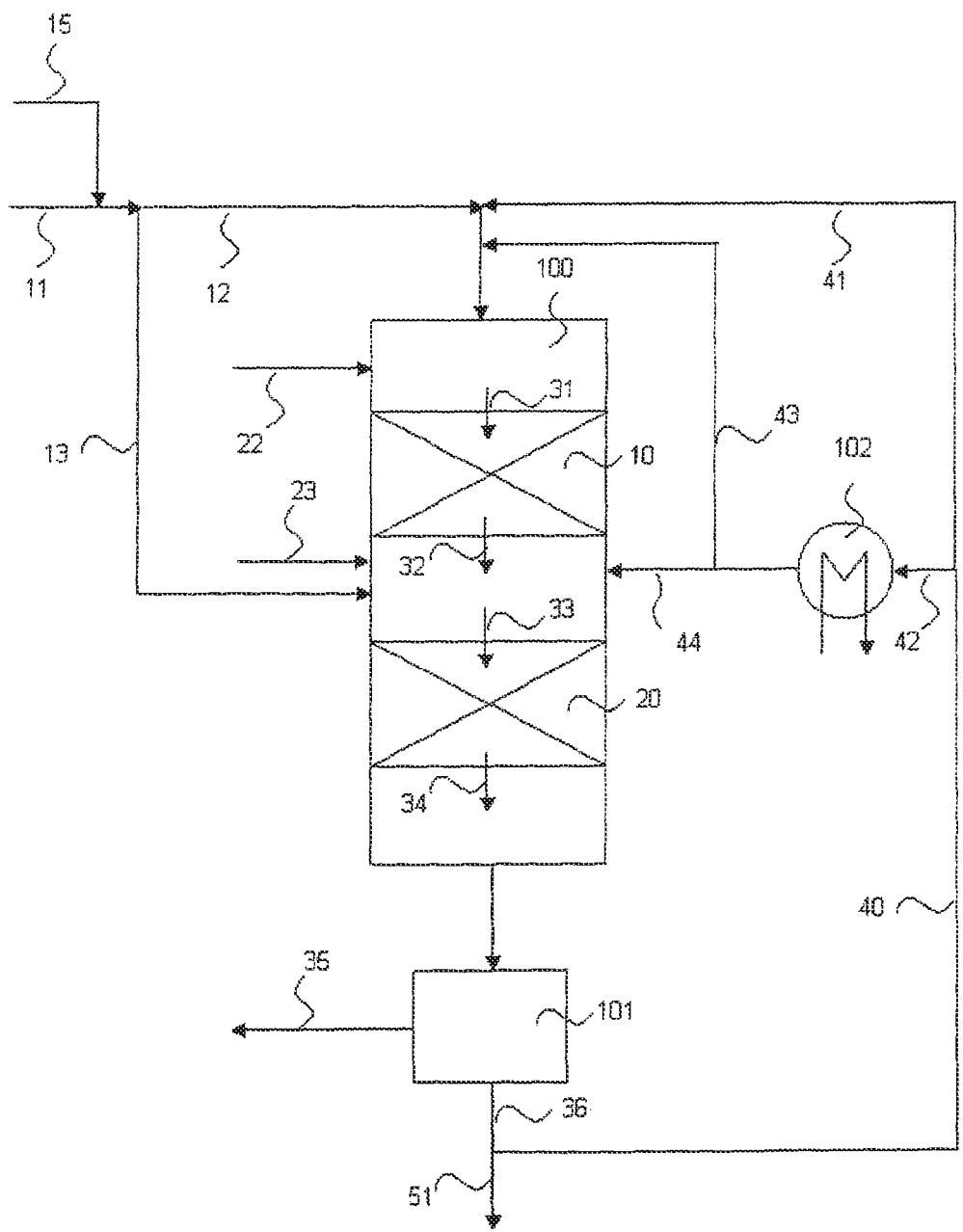
FIG. 1 schematically shows the operation of the hydrotreatment process.

A preferable embodiment of the invention and of the hydrotreatment step is illustrated in FIG. 1, wherein a hydrotreatment process configuration is provided, comprising one or more catalyst beds in series, hydrotreated product recycle introduction on the top of the first catalyst bed and fresh feed, quench liquid and hydrogen introduction on top of each catalyst beds. This results in improved control of the reaction temperature in the catalyst beds and hence diminishes undesired side reactions.

In FIG. 1 the hydrotreatment reactor 100 comprises two catalyst beds 10 and 20. Fresh feed 11 is introduced as streams 12 and 13 on the catalyst beds 10 and 20, respectively, and hydrogen as stream 22 and 23 on the catalyst beds 10 and 20, respectively. The fresh feed stream 12 is first mixed with the hydrotreated product recycle stream 41 and quench liquid stream 43 and the resulting mixture 31, diluted in the fresh feed concentration, is then introduced on the catalyst bed 10. In order to obtain a required sulphur concentration in the feed stream 31, required amount of sulphur make up is added to the fresh feed stream 11 via stream 15. As mixture 31 passes through the catalyst bed 10 with the hydrogen stream 22, fatty acids and fatty acid derivatives of the fresh feed stream 12 are converted to the corresponding reaction products. A two-phase stream 32 is withdrawn from the bottom of the catalyst bed 10 and is mixed with the fresh feed stream 13, quench liquid stream 44 and the hydrogen stream 23. The formed vapor-liquid mixture 33, diluted in the fresh feed concentration, is then introduced on the catalyst bed 20 at reduced temperature due to cooling effect of the hydrogen, quench liquid and fresh feed, passed through the catalyst bed 20 and finally withdrawn from the catalyst bed as a product stream 34. The stream 34 is separated in to a vapor stream 35 and liquid stream 36 in the high temperature separator 101. Vapor stream 35 is rich in hydrogen and is directed to further treatment. Part of the liquid stream 36 is returned to the reactor 100 as recycle stream 40, which is further divided to dilution stream 41 and total quench liquid stream 42. The quench liquid stream 42 is cooled in the heat exchanger 102 to provide adequate cooling effect on the top of the catalyst beds 10 and 20. Hydrotreated product stream 51 is directed from the hydrotreatment step to further processing.

The catalyst beds 10 and 20 may be located in the same pressure vessel or in separate pressure vessels. In the embodiment where the catalyst beds are in the same pressure vessels the hydrogen streams 22 and 23 may alternatively be introduced on the catalyst bed 10 and then be passed through the catalyst beds 10 and 20. In the embodiment where the catalyst beds are in separate pressure vessels, the catalyst beds may operate in parallel mode with separate dilution streams, hydrogen streams and quench liquid streams. The number of catalyst beds may be one or two or more than two.

The sulphur make up to the hydrotreatment step may be introduced with the fresh feed stream 11. Alternatively, required amount of sulphur may be fed with the hydrogen streams 22 and 23 as gaseous sulphur compound such as hydrogen sulphide.

Hydrogen is fed to the hydrotreating reactor in excess of the theoretical hydrogen consumption. During the hydrotreating step, triglyceride oils, fatty acids and derivatives thereof are almost theoretically converted to n-paraffins without or almost without side reactions. Additionally, propane is formed from the glycerol part of the triglycerides, water and CO and/or $CO_2$ from carboxylic oxygen, $H_2S$ from organic sulphur compounds and $NH_3$ from organic nitrogen compounds. Using the above described procedures in the hydrotreating step, the temperature needed for reactions to start up is achieved in the beginning of each catalyst bed, the temperature increase in the catalyst beds is limited, harmful and partially converted product intermediates can be avoided and the catalyst life is extended considerably. The temperature at the end of the catalyst bed is controlled by net heat of reactions and to the extent of the dilution agent used. The dilution agent may be any hydrocarbon available, of biological origin or non-biological origin. It can also be recycled product from the process. Fresh feed content from feed (total feed) is be less than 20 wt-%. If the product recycle is used, product recycle/fresh feed ratio is 5-30:1, preferably 10-30:1, most preferably 12-25:1. After the hydrotreatment step, the product is subjected to an isomerization step.

Feedstock

The bio oil and/or fat used as the fresh feed in the process of the present invention originates from renewable sources, such as fats and oils from plants and/or animals and/or fish and compounds derived from them. The basic structural unit of a typical plant or vegetable or animal oil/fat useful as the feedstock is a triglyceride, which is a triester of glycerol with three fatty acid molecules, having the structure presented in the following formula I:

Formula 1

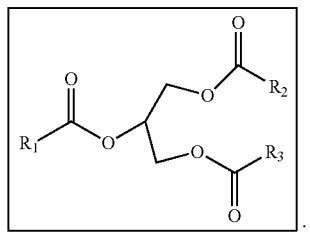

Structure of triglyceride

In formula I $R_1$, $R_2$ and $R_3$ are alkyl chains. Fatty acids found in natural triglycerides are almost solely fatty acids of even carbon number. Therefore $R_1$, $R_2$, and $R_3$ typically are $C_5$-$C_{23}$ alkyl groups, mainly $C_{11}$-$C_{19}$ alkyl groups and most typically $C_{15}$ or $C_{17}$ alkyl groups. $R_1$, $R_2$, and $R_3$ may contain carbon-carbon double bonds. These alkyl chains can be saturated, unsaturated or polyunsaturated.

Suitable bio oils are plant and vegetable oils and fats, animal fats, fish oils, and mixtures thereof containing fatty acids and/or fatty acid esters. Examples of suitable materials are wood-based and other plant-based and vegetable-based fats and oils such as rapeseed oil, colza oil, canola oil, tall oil, sunflower oil, soybean oil, hempseed oil, olive oil, linseed oil, mustard oil, palm oil, peanut oil, castor oil, coconut oil, as well as fats contained in plants bred by means of gene manipulation, animal-based fats such as lard, tallow, train oil, and fats contained in milk, as well as recycled fats of the food industry and mixtures of the above. Bio oil and fat suitable as fresh feed may comprise $C_{12}$-$C_{24}$ fatty acids, derivatives thereof such as anhydrides or esters of fatty acids as well as triglycerides of fatty acids or combinations of thereof. Fatty acids or fatty acid derivatives, such as esters may be produced via hydrolysis of bio oils or by their fractionalization or transesterification reactions of triglycerides.

In order to avoid catalyst deactivation and undesired side reactions the feed shall comply with the following requirements: The amount of alkaline and alkaline earth metals, calculated as elemental alkaline and alkaline earth metals, in the feed is below 10, preferably below 5 and most preferably below 1 w-ppm. The amount of other metals, calculated as elemental metals, in the feed is below 10, preferably below 5 and most preferably below 1 w-ppm. The amount of phosphorus, calculated as elemental phosphorus is below 30, preferably below 15 and most preferably below 5 w-ppm.

In many cases the feedstock, such as crude plant oil or animal fat, is not suitable as such in processing because of high impurity content and thus the feedstock is preferably purified using suitably one or more conventional purification procedures before introducing it to the hydrotreating step of the process. Examples of some conventional procedures are provided below:

Degumming of plant oils/fats and animal oils/fats means the removal of phosphorus compounds, such as phospholipids. Solvent extracted vegetable oils often contain significant amounts of gums, typically 0.5-3% by weight, which are mostly phosphatides (phospholipids) and therefore a degumming stage is needed for crude plant oils and animal fats in order to remove phospholipids and metals present in crude oils and fats. Iron and also other metals may be present in the form of metal-phosphatide complexes. Even a trace amount of iron is capable of catalysing oxidation of the oil or fat.

Degumming is performed by washing the feed at 90-105° C., 300-500 kPa(a), with $H_3PO_4$, NaOH and soft water and separating the formed gums. A major amount of metal components, which are harmful for the hydrotreatment catalyst, are also removed from the feedstock during the degumming stage. The moisture content of the degummed oil is reduced in dryer at 90-105° C., 5-50 kPa(a).

A feedstock, which is optionally degummed or refined in another conventional way, may be bleached. In the bleaching the degummed or refined feedstock is heated and mixed with natural or acid-activated bleaching clay. Bleaching removes various impurity traces left from other pretreatment steps like degumming, such as chlorophyll, carotenoids, phosphoipids, metals, soaps and oxidation products. Bleaching is typically carried out under vacuum to minimize possible oxidation. Generally the goal of bleaching is to reduce the color pigments in order to produce an oil of acceptable color and to reduce the oxidation tendency of oil.

Optionally the triglyceride structures of the feedstock may be decomposed by prehydrogenating the double bonds using reduced reaction temperature with NiMo or other catalyst, prior to the of by hydrodeoxygenations in order to prevent double bond polymerisation of unsaturated triglycerides.

The process according to the invention is particularly advantageous when the fresh feed contains more than 5% of free fatty acids and even more than 10% of free fatty acids. Thus also naturally occurring fats and oils containing significant amounts of free fatty acids can be processed without the removal of free fatty acids.

In the following the process according to the invention comprising a hydrotreating step and an isomerisation step is described in more detail.

Hydrotreating of Bio Oils and Fats

In the first step of the process, i.e. in the hydrotreating step, fatty acids, triglycerides and other fatty acid derivatives comprised in the feed are deoxygenated, denitrogenated and desulphurisated.

The feed comprises fresh feed and at least one dilution agent and the ratio of the dilution agent/fresh feed is 5-30:1, preferably 10-30:1, most preferably 12-25:1.

The dilution agent is selected from hydrocarbons and recycled product of the process i.e. product recycle or mixtures thereof.

In the hydrotreating step, the pressure range may be varied between 20 and 150 bar, preferably between 50 and 100 bar, and the temperature between 200 and 400° C., preferably between 250 and 350° C. and most preferably between 280 and 340° C.

It was found that the selectivity of decarb-reactions and the deoxygenation through decarb-reactions can be promoted during hydrotreating over the hydrotreatment catalyst, by using sulphur content of 50-20000 w-ppm, preferably 1000-8000 w-ppm, most preferably 2000-5000 w-ppm of sulphur in the total feed, calculated as elemental sulphur. The specific sulphur content in the feed is able to double the extent of n-paraffins formed by removal of COx. Complete deoxygenation of triglycerides by decarb-reactions can theoretically lower the consumption of hydrogen about 60% (max) compared with pure deoxygenation by hydrogen.

At least one organic or inorganic sulphur compound may optionally be fed along with hydrogen or with the feed to achieve the desired sulphur content. The inorganic sulphur compound can be for example $H_2S$ or elemental sulphur or the sulphur compound may be an easily decomposable organic sulphur compound such as dimethyl disulphide, carbon disulfide and butyl thiol or a mixture of easily decomposable organic sulphur compounds. It is also possible to use refinery gas or liquid streams containing decomposable sulphur compounds.

In the hydrotreatment/hydrodeoxygenation step, known hydrogenation catalysts containing metals from Group VIII and/or VIB of the Periodic System may be used. Preferably, the hydrogenation catalysts are supported Pd, Pt, Ni, NiMo or a CoMo catalyst, the support being alumina and/or silica, as described for instance in FI 100248. Typically, NiMo/$Al_2O_3$ and CoMo/$Al_2O_3$ catalysts are used.

In order to control the increase of temperature resulting from the aforementioned reactions over catalyst beds and side reaction formation, an improved reactor configuration is presented in FIG. 1. The hydrotreatment section comprises one or more catalyst beds in series, dilution agent introduction on the top of the first catalyst bed and fresh feed, recycle liquid and hydrogen introduction on top of each catalyst beds. If the dilution agent is product recycle, the product recycle/fresh oil-ratio is from 5-30:1, preferably 10-30:1 and most preferably 12-25:1. The catalyst beds can be located in same pressure vessel or each bed in a separate pressure vessel. Hydrogen is fed in excess to the theoretical chemical hydrogen consumption and the feedstock is converted totally or almost totally within each catalyst bed. Using these procedures, harmful, partially converted product intermediates are avoided, the temperature needed for reaction initiation is achieved in the beginning of each catalyst bed, the rise of reaction heating is controlled in the catalyst beds and the catalyst life is improved considerably.

Hydrodeoxygenation of triglycerides facilitates controlled decomposition of the triglyceride molecule contrary to uncontrolled cracking. Double bonds are also hydrogenated during the controlled hydrotreatment. Light hydrocarbons and gases formed, mainly propane, water, $CO_2$, CO, $H_2S$ and $NH_3$ are removed from the hydrotreated product.

It was surprisingly observed in examples that product recycle dilution can prevent or remarkably decrease the reactions between free fatty acids and the formation of high molecular weight compounds during hydrotreating, when at least 5:1 (product recycle):(fresh oil)-ratio was used. The effect of product recycle is based on two phenomena: dilution effect of recycle and more controllable and reduced reaction temperatures used over catalyst bed during hydrodeoxygenation. Higher temperatures and especially hot spots of catalyst bed promote ketonisation reactions. Due to this invention, it is possible to use various sources of bio oils and fats without the need to remove fatty acids. After the hydrotreatment step, the product is subjected to an isomerization step.

Isomerisation of n-Paraffins Formed During Hydrotreatment

In the second step of the process, i.e. in the isomerization step, isomerization is carried out which causes branching of the hydrocarbon chain and results in improved performance of the product oil at low temperatures. The isomerisation produces predominantly methyl branches. The severity of isomerisation conditions and choice of catalyst controls the amount of methyl branches formed and their distance from each other and therefore cold properties of bio diesel fraction produced. The product obtained from the hydrotreatment step is isomerised under isomerisation conditions with an isomerisation catalyst.

In the process according to the invention, the feed into the isomerisation reactor is a mixture of pure n-paraffins and the composition of it can be predicted from the fatty acid distribution of individual bio oils. During the hydrotreating step of the process, triglyceride oils and other fatty acid derivatives and fatty acids are almost theoretically converted to n-paraffins. Additionally propane is formed from the glycerol part of triglycerides, water and COx from carboxylic oxygen, $H_2S$ from organic sulphur compounds and $NH_3$ from organic nitrogen compounds. It is substantial for the process that these gas phase impurities are removed as completely as possible before the hydrocarbons are contacted with the isomerization catalyst.

The isomerization step may comprise an optional stripping step, wherein the reaction product from the hydrotreatment step may be purified by stripping with water vapour or a suitable gas such as light hydrocarbon, nitrogen or hydrogen. The optional stripping step is carried out in countercurrent manner in a unit upstream of the isomerization catalyst, wherein the gas and liquid are contacted with each other, or before the actual isomerization reactor in a separate stripping unit utilizing the counter-current principle.

In the isomerisation step, the pressure varies in the range of 20-150 bar, preferably in the range of 30-100 bar and the temperature varies between 200 and 500° C., preferably between 280 and 400° C.

In the isomerisation step, isomerisation catalysts known in the art may be used. Suitable isomerisation catalysts contain a molecular sieve and/or a metal selected from Group VIII of the Periodic Table and/or a carrier. Preferably, the isomerisation catalyst contains SAPO-11 or SAPO-41 or ZSM-22 or ZSM-23 or ferrierite and Pt, Pd or Ni and $Al_2O_3$ or $SiO_2$. Typical isomerization catalysts are, for example, Pt/SAPO-11/$Al_2O_3$, Pt/ZSM-22/$Al_2O_3$, Pt/ZSM-23/$Al_2O_3$ and Pt/SAPO-11/$SiO_2$. Most of these catalysts require the presence of hydrogen to reduce the catalyst deactivation.

An isomerised product, which is a mixture of branched hydrocarbons and preferably branched paraffins boiling in the range of 180-350° C., the diesel fuel range, and having one carbon atom less than the original fatty acid chain, is obtained. Additionally some gasoline and gas may be obtained.

Advantages of the Invention

The invention provides a method for reducing the formation of higher molecular weight compounds during the hydrotreatment of a feed obtained from plant oils and animal fats and which may contain free fatty acids.

It was surprisingly found that the problems of prior art processes may be avoided or at least significantly reduced by the improved process according to the invention, comprising a hydrotreatment step and an isomerisation step wherein product recycle or another dilution agent in the hydrotreatment step in combination with reduced operation temperature result in important improvements, particularly when the fresh feed contains more than 5 wt % of free fatty acids. A special reactor configuration and high dilution of fresh feed introduced into hydrotreatment are used in the method. The extent of side reactions is decreased and the stability of catalyst during hydrotreating is increased during the hydrotreatment step.

In the examples it was be seen that the ratio of at least 5:1 (recycle:fresh) significantly decreased the formation of high molecular weight products, when the feedstock contains 10 wt-% of free fatty acids (calculated from fresh oil) is used. Using at least 5:1 recycle ratio and reduced reaction temperature, free fatty acids can be processed without the need for deacidification. High quality hydrocarbons are obtained, suitable for the diesel fuel pool with high yield.

The invention is illustrated in the following with examples presenting some preferable embodiments of the invention. However, it is evident to a man skilled in the art that the scope of the invention is not meant to be limited to these examples.

EXAMPLES

All hydrotreatment tests were performed in the presence of hydrogen.

Example 1. Comparative Example

Tali Oil Feed (100% Free Fatty Acids) without Product Recycle

Figure 8:
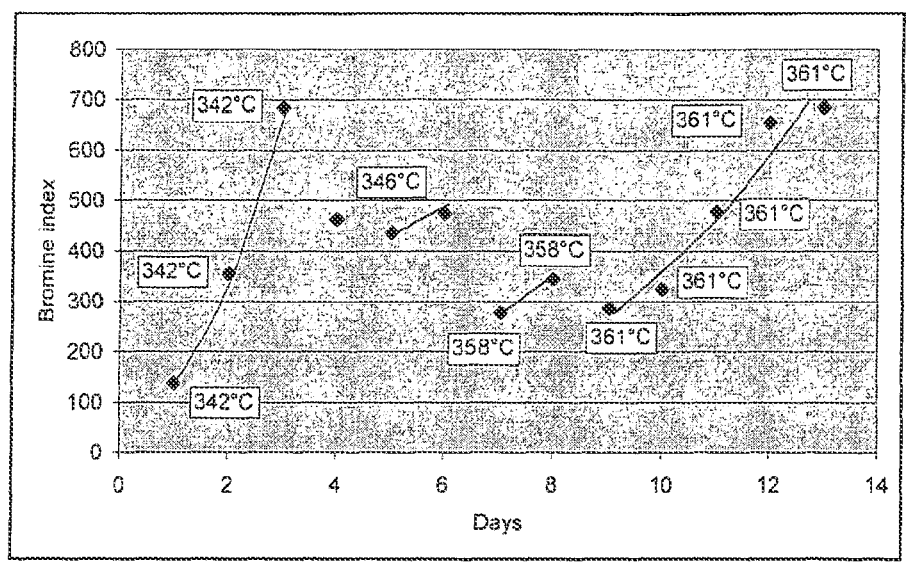
FIG. 8 shows that the bromine indexes increased during run even if temperature compensation of catalyst was used.

Hydrotreating of tall oil (100% free fatty acids) with NiMo catalyst was carried out at 50 bars pressure, LHSV 1.5 and reaction temperatures from 340-360° C. without product recycle. Hydrogen oil ratio was 900 normal liters $H_2$ per liter oil fed. The hydrotreating of tall oil 100% free fatty acid feed caused rapid deactivation of NiMo catalyst, and formation of heavy weight compounds and aromatics was observed. Bromine indexes increased during the run even if temperature compensation of catalyst was used (FIG. 8). Product oil contained about 7 wt-% aromatics and about 7 wt-% heavies (>375° C. boiling). Density (50° C.) of product oil was high 777.1 kg/m3 compared to typical values with rapeseed oil hydrotreated product oil (761-762 kg/m3) using lower reaction temperature and optimized reaction conditions.

Example 2. Comparative Example

Tall Oil Fatty Acid Feed (100% FFA) at High Reaction Temperatures without Product Recycle Hydrotreating of tall oil fatty acid feed (100% FFA) at high reaction temperatures 370-385° C. was carried out without product recycle. Rapid deactivation of NiMo catalyst and formation of heavy weight compounds and aromatics was observed. Density of hydrotreated oil (table 1) was significantly higher than in rapeseed oil runs (typically 761-762 kg/m3). Both oils contained mainly C18 fatty acids (~90-wt-%) and rather steady formation of water was observed during run. During the tall oil hydrotreating about 7-8 wt-% heavier molecular weight compounds and 8.1 wt-% aromatics were formed. These side reactions are caused by concentrated fatty acid feed and too high reaction temperatures. Deactivation of catalyst is clearly seen from increasing bromine indexes. During the satisfactory operation bromine index should be below 50. Table 1 describes densities, bromine indexes, reaction temperatures and water formed during test runs for 2 to 14 days using tall oil fatty acid feed (100% FFA) without recycling.

TABLE 1

| | Duration of test run | | | | | | | |
|---|---|---|---|---|---|---|---|---|
| | 2nd day | 4th day | 6th day | 9th day | 11th day | 12th day | 13th day | 14th day |
| Temperature, ° C. | 370 | 375 | 378 | 381 | 385 | 385 | 385 | 385 |
| Density, 50° C., kg/m3 | 771.8 | 773.1 | 773.7 | 776.5 | 779.1 | 779.8 | 780.5 | 781.2 |
| Bromine index | 101 | 150 | 188 | 198 | 247 | 269 | 300 | 330 |
| Product water, % | 9.37 | 9.5 | 9.81 | 10.3 | 10.2 | 10.0 | 10.1 | 10.2 |

Example 3. Comparative Example

Effect of Metal Impurities of Bio Oils on the Catalyst Performance

Tube reactor hydrotreatment test runs were carried out using crude rapeseed oil, crude animal fat and purified rapeseed oil. Analysis of these feeds are shown in Table 2. Crude feeds contained significant amount of metals, organic phosphorus, sulphur and nitrogen compounds. Purified feeds contained only trace levels of these impurities

TABLE 2

Impurity levels of crude and purified plant oils and animal fats

| Impurity | Unit | Crude Rapeseed oil | Purified Rapeseed oil | Crude Animal fat |
|---|---|---|---|---|
| Metals (total) | ppm | 90 | ~0 | 162 |
| Org.nitrogen | ppm | 33 | 7.2 | 1125 |
| Free Fatty acid, GPC | Wt-% | 0.8 | 0.7 | 10.8 |
| Total Acid Number | mg KOH/g | 1.0 | 0.1 | 21.5 |
| Phosphorous | ppm | 110 | <1 | 86 |
| Sulphur (original) | ppm | 3 | 1 | 85 |

Figure 4:
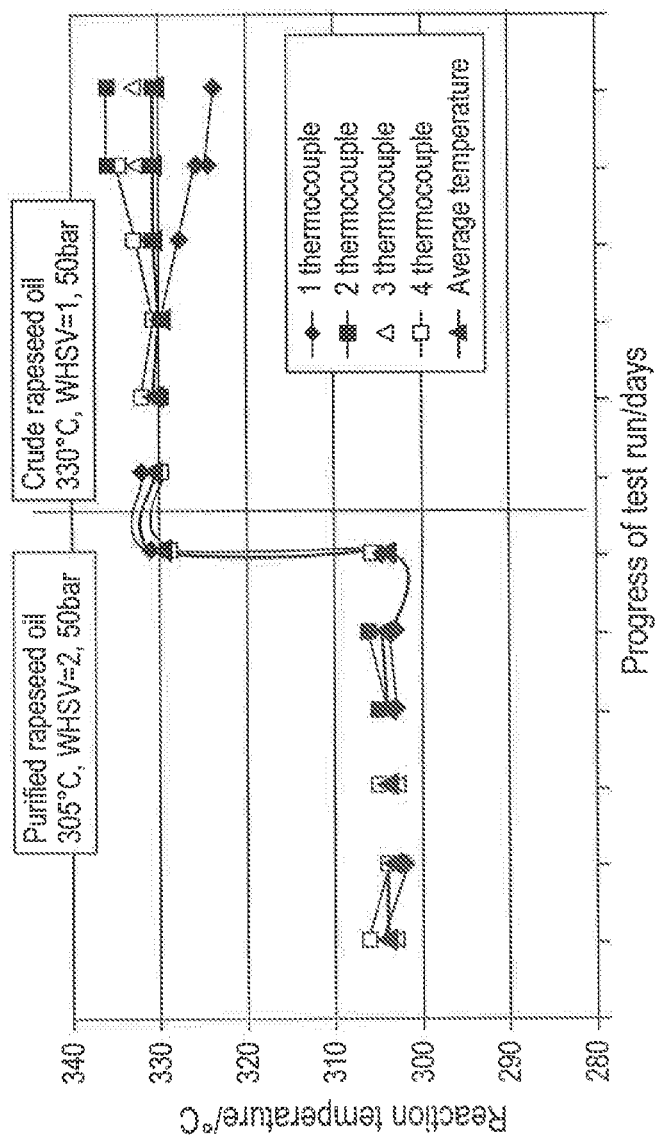
FIG. 4 shows reaction temperature profile over catalyst bed and performance of crude rapeseed oil.
Figure 5:
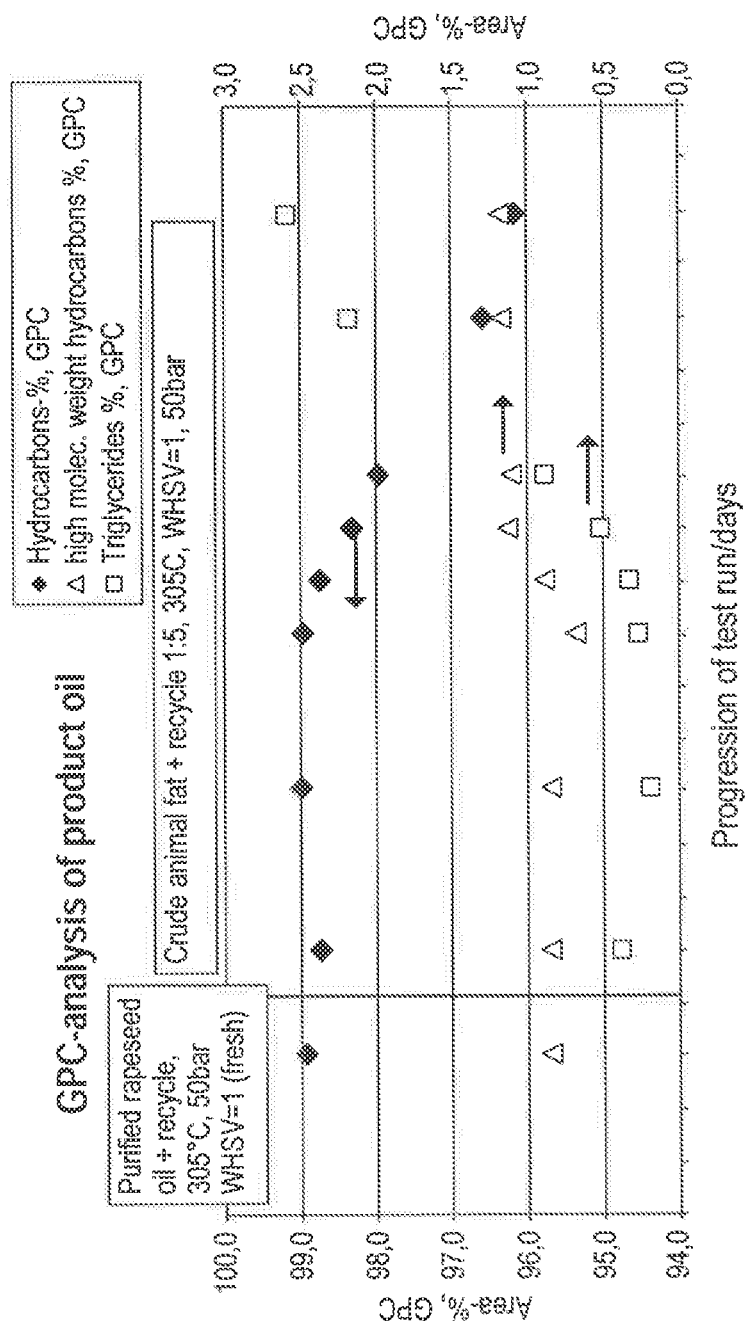
FIG. 5 shows performance of crude animal fat.

Test runs using crude, unpurified oils/fats showed that catalyst needed higher temperatures to work properly, but gradually lost its activity (FIG. 5). Triglycerides and increased bromine number of product oil was found. High amount of metals were also detected on to the catalyst. Temperature profile of the catalyst bed showed that top of the catalyst bed was deactivated and reaction section moved forward (FIG. 4), when reactor heating was maintained steady. Metals adsorbed on to the catalyst also promote side reactions like decarb-reactions.

First hydrotreatment test run was carried out using crude rapeseed oil. Purified rapeseed oil was used as a reference feed. Purified rapeseed oil achieved complete HDO conversion at 305° C. using WHSV=2. Crude rapeseed oil gave total HDO conversion not until reaction temperature 330° C. was used with space velocity WHSV=1. It was however seen from temperature profiles over the catalyst bed that first part of catalyst was deactivated very quickly. In FIG. 4, reaction temperature profile over catalyst bed and performance of crude rapeseed oil are presented.

Second hydrotreatment test run was carried out using purified rapeseed oil and crude animal fat. Purified rapeseed oil was used as a reference feed. Purified rapeseed oil with product recycle achieved complete HDO conversion at 305° C. using WHSV=1. Crude animal fat with product recycle did not give complete HDO conversion at 305° C. using WHSV=1. It was seen from GPC analyses that product oil contained triglycerides and catalyst also significantly deactivated during crude animal fat feed. Pumping problems was also observed during crude animal fat feeding. Performance of crude animal fat is presented in FIG. 5.

Example 4. Comparative Example

Figure 2:
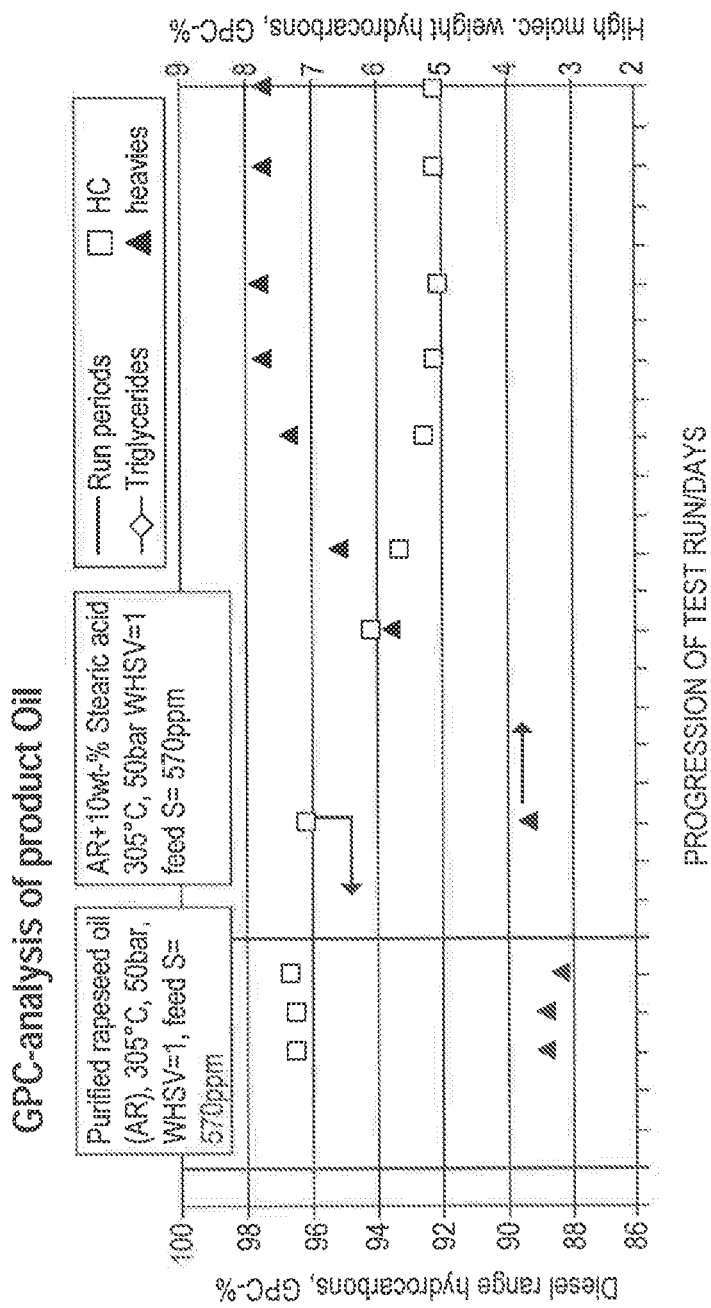
FIG. 2 shows the increase of formation of high molecular weight hydrocarbons when 10 wt-% free fatty acids was fed along with purified rapeseed oil triglycerides without product recycle.

Effect of Free Fatty Adds (10 wt-% in Fresh Feed) on the Formation of High Molecular Weight Hydrocarbons Hydrotreatment was carried out using purified rapeseed oil as reference feed without product recycle. A test run was carried out at 305° C. and 50 bars pressure using WHSV=1 and $H_2$/oil-ratio=1000. Sulphur content of feed was 570 ppm. During a second hydrotreatment test period stearic acid was fed (10 wt-% from rapeseed oil) along with purified rapeseed oil using same reaction conditions without product recycle. It was right away observed that the extent of high molecular weight compounds increased gradually from initial level ~3 wt-% to ~8 wt-%. These higher molecular weight compounds (molecular weight double or more of the feed) are not in the boiling range of diesel fuel and thus decrease diesel yield and potentially shorten the catalyst life. Thus free fatty acids in bio oils make their processing more difficult. In FIG. 2 the increase of formation of high molecular weight hydrocarbons is observed, when 10 wt-% free fatty acids was fed along with purified rapeseed oil triglycerides without product recycle.

Example 5

Effect of Product Recycle on Preventing Formation of Unwanted Heavy Side Reaction Compounds when the Feed Contained 10 wt-% Free Fatty Acids A hydrotreatment test run was carried out using 10 wt-% stearic acid containing purified rapeseed oil as reference feed without product recycle under following reaction conditions: WHSV=1.50 bars, 305° C., H2/oil-ratio=1000 and sulphur content of feed=570 ppm. During the second hydrotreatment test run period same feed was diluted with product hydrocarbons so that (fresh oil)/(product recycle)-ratio was 1:5. WHSV of fresh oil was maintained at 1, therefore WHSV of total oil feed increased to 6. The reaction temperature was kept at 305° C. and reaction pressure at 50 bars. $H_2$/(fresh oil)-ratio was maintained at 1000. HDO product (n-paraffins) simulated product recycle, which was mixed in advance with fresh oil. The initial content of heavy hydrocarbons in the recycle was ~0.4 wt-%.

Figure 3:
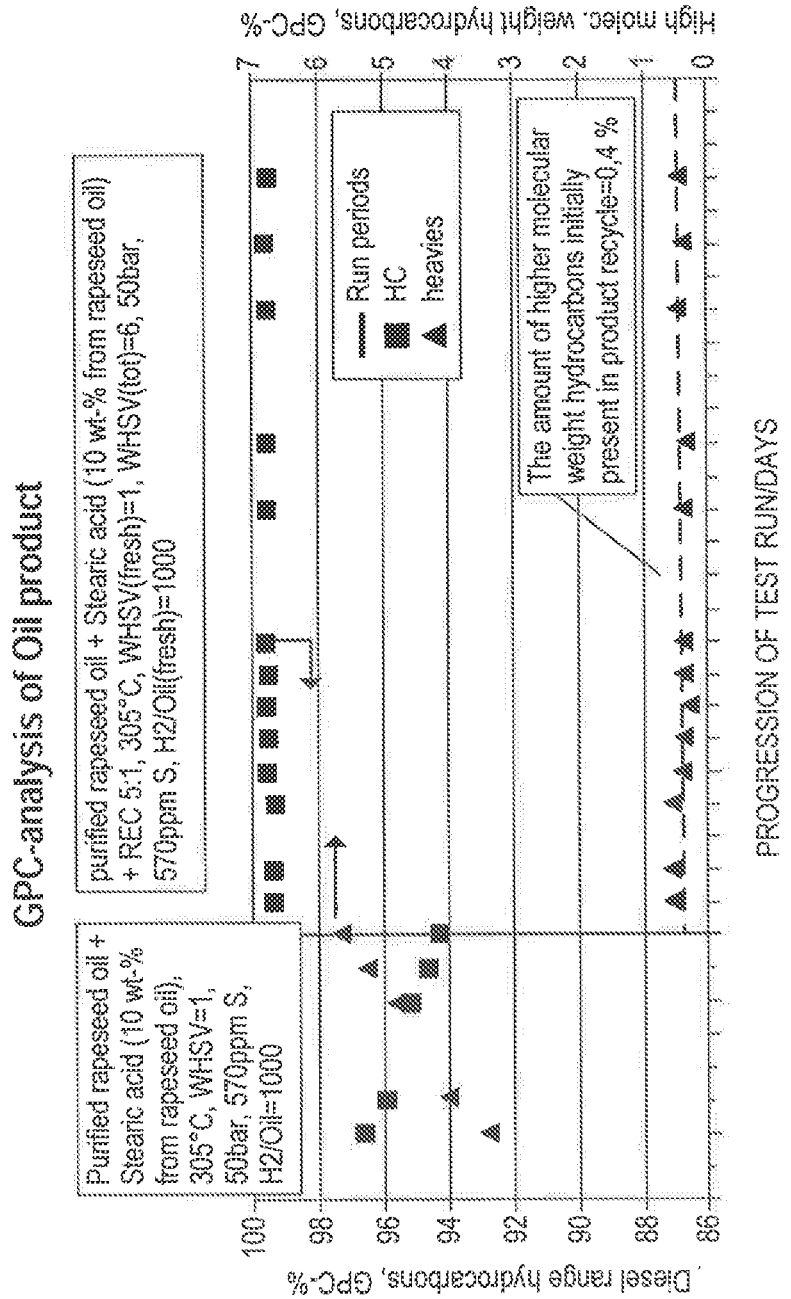
FIG. 3 shows the effect of product recycle on preventing the formation of unwanted higher molecular weight by-product.

It was unexpectedly observed that the formation of heavy hydrocarbons was almost totally prevented or at least very significantly decreased when product recycle was used (FIG. 3). This is most probably caused by significantly diminished side reactions of free fatty acids wherein a carboxylic acid molecule can react with another carboxylic acid molecule to form a higher molecular weight compounds. In FIG. 3 the effect of product recycle on preventing the formation of unwanted higher molecular weight by-product is presented. Table 3 presents analysis results of the feed and products.

TABLE 3

Analysis results of the feed and products

| | | | Feed analyses | | | Product analyses | | |
|---|---|---|---|---|---|---|---|---|
| | | | | | | AR + 10 | AR + 10 | AR + 10 |
| Property | Method | Units | AR | Recycle feed | AR (10% SA) | AR (10% SA) + REC 1:5 | wt-% stearic acid without recycle | wt-% SA + Recycle after 196 hours | wt-% SA + Recycle after 552 hours |
| Density, 15° C. calc. | D 4052 | kg/m³ | 920.4 | 788.1 | 915.8 | 807.2 | 790.8 | 788.3 | 788.3 |
| Density, 50° C. | D 4053 | kg/m³ | 897.6 | 761.4 | 893.2 | 781.2 | 764.2 | 761.7 | 761.7 |
| Br-index | D 2750 | mg/100 g | | 53.7 | | | 21.5 | | 26 |
| Br number | D 1159 | g/100 g | 56 | | 49.1 | 6.3 | | | |
| Iodinenumber | D 5554 | g/100 g | 112 | | 103 | 18 | | | |
| HC | GPC | area-% | | 99.6 | | 83.0 | 94.3 | 99.6 | 99.6 |
| Fatty acids | GPC | area-% | 0.7 | 0 | 10.6 | 1.8 | 0 | 0 | 0 |
| Heavy HC | GPC | area-% | 0 | 0.4 | | 0.5 | 5.7 | 0.4 | 0.4 |
| Diglycerides | GPC | area-% | 2.3 | 0 | 2.4 | | 0 | 0 | 0 |
| Triglycerides | GPC | area-% | 97 | 0 | 87 | 14.7 | 0 | 0 | 0 |

SA = Stearic acid,
AR = purified rapeseed oil,
REC = product recycle,
HC = hydrocarbons,
heavy HC = high molecular weight hydrocarbons Example 6. Comparative Example The Effect of Lower Reaction Temperature on the Selectivity of n-Paraffins and Oil Yield Studies were carried out with NiMo catalyst using rapeseed oil as feed and reaction temperatures 280-330° C. and 340-360° C., WHSV=1 and reactor pressure of 50 bars. Alkali raffinated rapeseed oil triglycerides contained mainly $C_{18}$ fatty acids. $C_{18}$ fatty acids contributed about 89 wt-% of all fatty acids in rapeseed oil. Theoretical amount of n-paraffins formed from rapeseed oil fed is about 86.4 wt-% (calculated from rapeseed oil fed).

Figure 6:
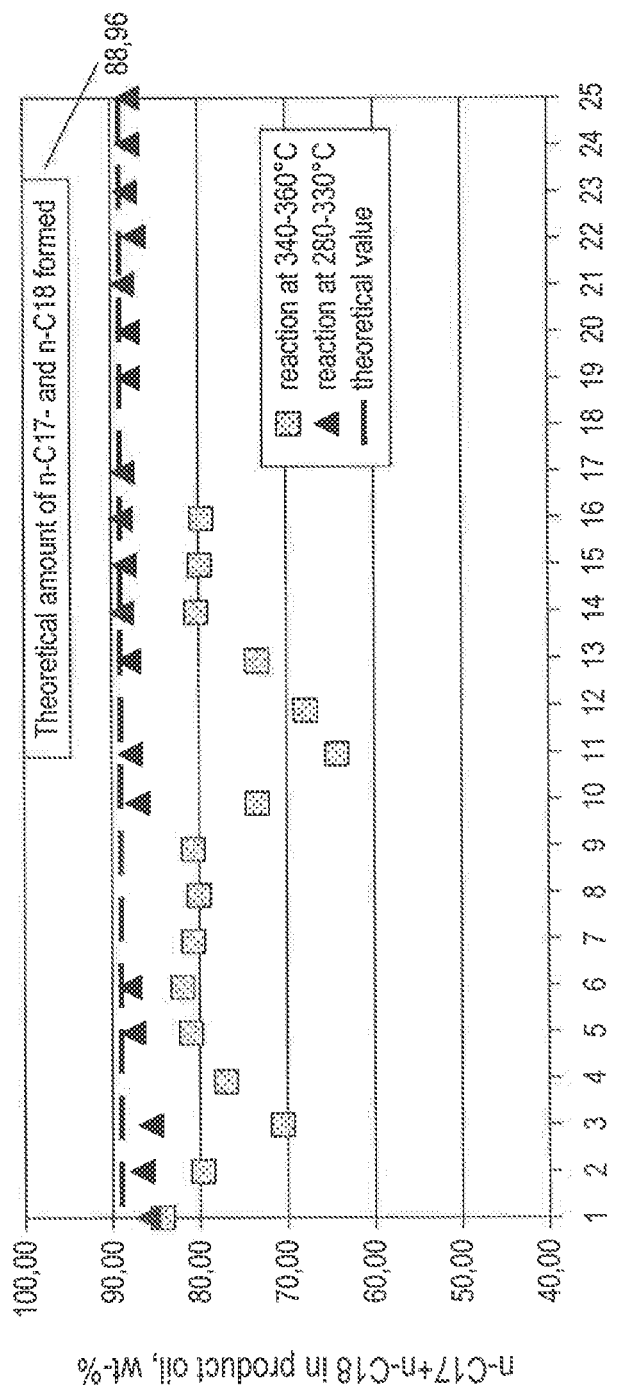
FIG. 6 shows the conversion of rapeseed oil triglycerides to n-paraffins.

Complete HDO conversion with almost theoretical n-paraffin yield was accomplished, when well controlled reaction temperatures <330° C. were used. Almost theoretical n-paraffin yields tell us from complete HDO conversion and very controllable operation without significant side reactions. High amount of side reactions (cyclisation, aromatisation and cracking) and low n-paraffin yield were observed when unnecessary high reaction temperatures 340-360° C. was used. In FIG. 6 the conversion of rapeseed oil triglycerides to n-paraffins is presented.

Example 7

Stability of Catalyst

Figure 7:
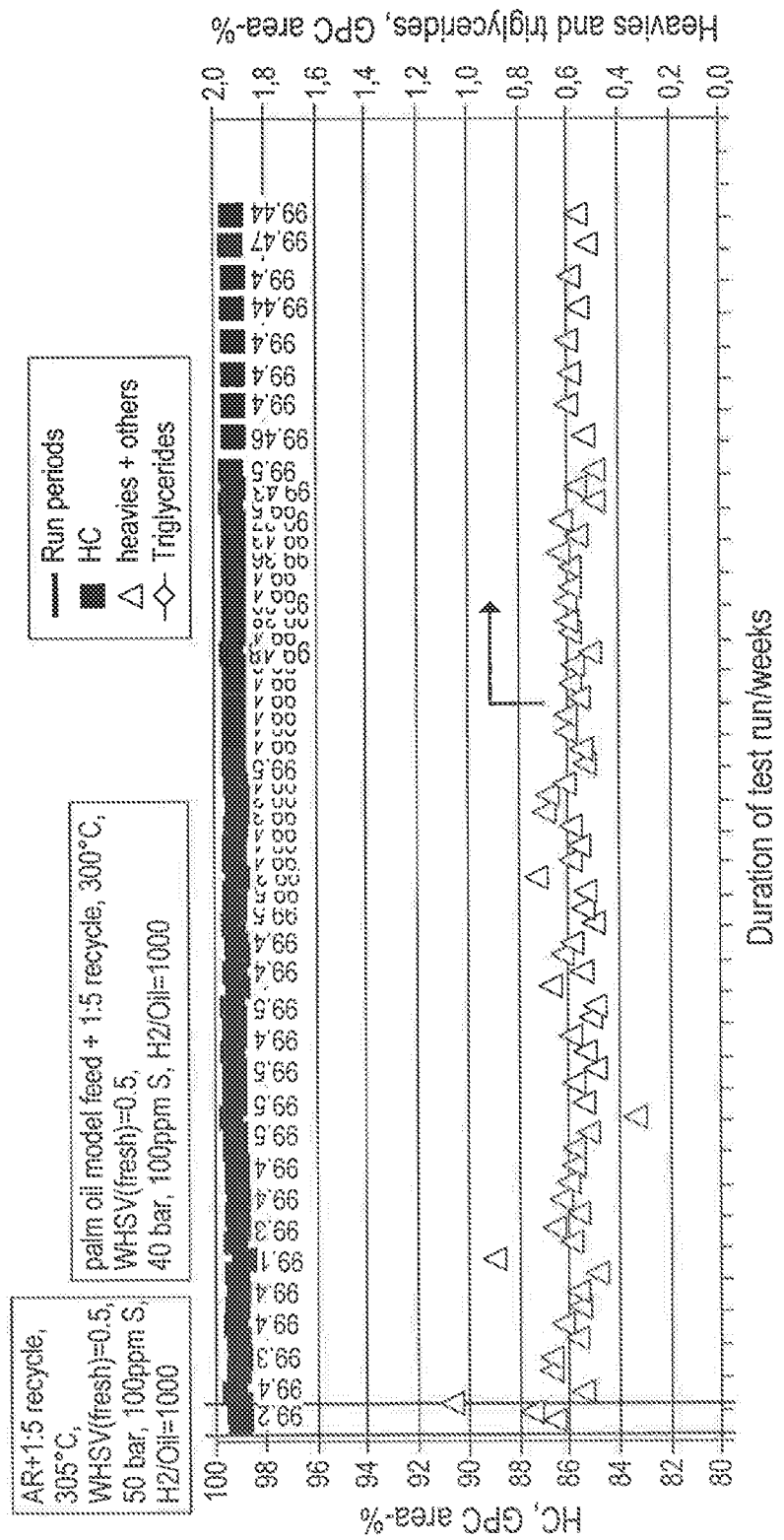
FIG. 7 shows the stability of catalyst as stabile operation was maintained and the formation of heavies was steady over the whole test run of over 9 months.

The stability of NiMo-catalyst using palm oil model feed (impurities added) along with product recycle (catalyst life test) was carried out using following reaction conditions: Reaction temperature=300-305° C., Reactor pressure=40 bars, WHSV (fresh)=0.5, WHSV (total)=3, $H_2$/Oil (fresh) =900, Sulphur in feed=100 w-ppm. Palm oil was used as a main component of feed, but it was modified with animal fat, fractions of free fatty acids, crude rapeseed oil, and lecithin in order to get suitable specification of impurities of test feed. Fresh feed analysis is presented below in table 4. Fresh oil was then diluted in advance with 1:5 ratio of HDO product (simulates product recycle). The duration of test run was over 9 months. Stabile operation was maintained (table 4 and FIG. 7) and the formation of heavies was steady over the whole test run FIG. 7.

TABLE 4

Stability of catalyst

| | | | | Product oil analysis Run duration | | | |
|---|---|---|---|---|---|---|---|
| Analysis | Method | Unit | Fresh Feed analysis | 383 hours | 1898 hours | 3408 hours | 5601 hours |
| Density, 15° C. | D 4052 | kg/m³ | 804.9 | 787.4 | 785.6 | 785.3 | 784.9 |
| Density, 50° C. | D 4052 | kg/m³ | 778.8 | 760.7 | 758.9 | 758.6 | 758.1 |
| Br-index | D 2710 | mg/100 g | 29200 | 33 | 48 | 33 | 11 |
| HC | GPC | area-% | 0 | 99.3 | 99.4 | 99.3 | 99.4 |
| Fatty acids | GPC | area-% | 1.2 | 0 | 0 | 0 | 0 |
| Monoglyc/high molec. weight HC | GPC | area-% | 0.3 | 0.7 | 0.6 | 0.7 | 0.6 |
| Diglycerides | GPC | area-% | 6.3 | 0 | 0 | 0 | 0 |
| Triglycerides | GPC | area-% | 92.1 | 0 | 0 | 0 | 0 |
| TAN | D664 | mg KOH/g | 2.1 | ~0 | ~0 | ~0 | ~0 |
| Sulphur | D 5453 | ppm | 3 | 1.2 | 2.0 | 2.7 | 2 |
| Nitrogen | D4629 | mg/kg | 6 | <1 | <1 | 1.2 | <1 |
| Sodium, oil | AAS | mg/kg | 3 | 0.4 | <0.1 | <0.1 | <0.1 |
| Calcium, oil | AAS | mg/kg | 2 | 0.3 | <0.1 | <0.1 | <0.1 |

TABLE 4-continued

Stability of catalyst

| Analysis | Method | Unit | Fresh Feed analysis | Product oil analysis Run duration | | | |
|---|---|---|---|---|---|---|---|
| | | | | 383 hours | 1898 hours | 3408 hours | 5601 hours |
| Magnesium, oil | AAS | mg/kg | 0.3 | <0.1 | <0.1 | <0.1 | <0.1 |
| Molybdenum, oil | AAS | mg/kg | — | <0.5 | <0.5 | <0.5 | <0.5 |
| Aluminum, oil | ICP metals | mg/kg | <2 | <2 | <2 | <2 | <2 |
| Iron, oil | ICP metals | mg/kg | <1 | <1 | <1 | <1 | <1 |
| Nickel, oil | ICP metals | mg/kg | <1 | <1 | <1 | <1 | <1 |
| Phosphorus, oil | ICP metals | mg/kg | 4 | <1 | <1 | <1 | <1 |

The invention claimed is:

1. A process for the manufacture of diesel-range branched hydrocarbons comprising the following steps:
   hydrotreating in one or more catalyst beds a feed comprising:
   (i) at least one organic or inorganic sulphur compound,
   (ii) hydrogen,
   (iii) a feedstock comprising bio oil and/or fat from renewable sources, and
   (iv) at least one diluting agent,
   in the presence of a hydrogenation catalyst to form hydrocarbons,
   wherein a reaction temperature at the beginning of each of the one or more catalyst beds is 280-330° C.;
   controlling a temperature at the end of each of the one or more catalyst beds by the addition of the at least one diluting agent to each of the one or more catalyst beds; and
   isomerizing the formed hydrocarbons in the presence of an isomerization catalyst to produce diesel-range branched hydrocarbons.

2. The process according to claim 1, wherein the hydrogen comprises fresh hydrogen.

3. The process according to claim 1, wherein the feedstock consists of bio oil and/or fat from renewable sources.

4. The process according to claim 3, wherein the at least one diluting agent consists of a diluting agent of biological origin.

5. The process according to claim 4, wherein the feed consists of:
   (i) the at least one organic or inorganic sulphur compound,
   (ii) the hydrogen,
   (iii) the feedstock consisting of bio oil and/or fat from renewable sources, and
   (iv) the diluting agent of biological origin.

6. The process according to claim 1, wherein the feedstock comprises a pretreated bio oil and/or fat.

7. The process according to claim 6, wherein the feedstock comprises a purified or prehydrogenated bio oil and/or fat.

8. The process according to claim 1, wherein the diluting agent comprises a recycled product from the isomerization step.

9. The process according to claim 1, wherein the diluting agent comprises a recycled product from the hydrotreatment step.

10. The process according to claim 9, wherein a ratio of the at least one diluting agent to the feedstock consisting of bio oil and/or fat from renewable sources is 5-30:1.

11. The process according to claim 1, wherein a temperature of the at least one diluting agent is controlled using a heat exchanger.

12. The process according to claim 1, wherein the reaction temperature at the beginning of each of the one or more catalyst beds is 300-305° C.

13. The process according to claim 1, wherein the feed is hydrotreated in two catalyst beds.

14. A process for the manufacture of diesel-range branched hydrocarbons comprising the following steps:
   hydrotreating in one or more catalyst beds a feed comprising:
   (i) at least one organic or inorganic sulphur compound,
   (ii) hydrogen,
   (iii) a feedstock comprising bio oil and/or fat from renewable sources, and
   (iv) at least one diluting agent,
   in the presence of a hydrogenation catalyst to form hydrocarbons,
   wherein a reaction temperature at the beginning of each of the one or more catalyst beds is 280-330° C., and
   wherein the feed contains less than 1 w-ppm alkali and alkaline earth metals, calculated as elemental alkali and alkaline earth metals, less than 1 w-ppm other metals, calculated as elemental metals, and less than 5 w-ppm phosphorous, calculated as elemental phosphorous;
   controlling a temperature at the end of each of the one or more catalyst beds by the addition of the at least one diluting agent to each of the one or more catalyst beds; and
   isomerizing the formed hydrocarbons in the presence of an isomerization catalyst to produce diesel-range branched hydrocarbons.

15. A process for the manufacture of diesel-range branched hydrocarbons comprising the following steps:
   hydrotreating in one or more catalyst beds a feed comprising:
   (i) at least one organic or inorganic sulphur compound,
   (ii) hydrogen,
   (iii) a feedstock comprising bio oil and/or fat from renewable sources, and
   (iv) at least one diluting agent,
   in the presence of a hydrogenation catalyst to form hydrocarbons,
   wherein a reaction temperature at the beginning of each of the one or more catalyst beds is 280-330° C., and
   wherein the feed contains 50-850 w-ppm of sulphur, calculated as elemental sulphur;
   controlling a temperature at the end of each of the one or more catalyst beds by the addition of the at least one diluting agent to each of the one or more catalyst beds; and isomerizing the formed hydrocarbons in the presence of an isomerization catalyst to produce diesel-range branched hydrocarbons.

* * * * *